(12) United States Patent
Wald et al.

(10) Patent No.: US 11,679,254 B2
(45) Date of Patent: Jun. 20, 2023

(54) SYSTEM AND METHOD FOR USING CONCOMITANT FIELDS TO CONTROL PERIPHERAL NERVE STIMULATION (PNS) IN MRI IMAGE ENCODING

(71) Applicant: THE GENERAL HOSPITAL CORPORATION, Boston, MA (US)

(72) Inventors: Lawrence Wald, Cambridge, MA (US); Bastien Guerin, Cambridge, MA (US); Mathias Davids, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 191 days.

(21) Appl. No.: 15/811,588

(22) Filed: Nov. 13, 2017

(65) Prior Publication Data

US 2018/0133467 A1 May 17, 2018

Related U.S. Application Data

(60) Provisional application No. 62/420,822, filed on Nov. 11, 2016.

(51) Int. Cl.
*A61B 5/055* (2006.01)
*A61B 6/00* (2006.01)
(Continued)

(52) U.S. Cl.
CPC .............. *A61N 1/086* (2017.08); *A61B 5/055* (2013.01); *A61B 6/469* (2013.01); *A61N 1/0551* (2013.01);
(Continued)

(58) Field of Classification Search
CPC .......... A61N 1/086; A61N 2/006; A61N 2/02; A61N 1/3605; A61N 1/0551; A61B 6/469;
(Continued)

(56) References Cited

U.S. PATENT DOCUMENTS

| 6,229,309 B1 * | 5/2001 | Aldefeld .......... G01R 33/56581 324/309 |
| 2010/0085048 A1 * | 4/2010 | Bouchard .............. G01R 33/48 324/307 |

(Continued)

OTHER PUBLICATIONS

Neufeld E, Cassara A, Montanaro H, Kainz W and Kuster N, "Functionalized anatomical models for em-neuron interaction modeling." Phys. Med. Biol. 61 4416-27 (Year: 2016).*

*Primary Examiner* — Bill Thomson
*Assistant Examiner* — Amal Aly Farag
(74) *Attorney, Agent, or Firm* — Quarles & Brady LLP

(57) ABSTRACT

A system and method is provided for assessing Peripheral Nerve Stimulation (PNS). The system receives an imaging pulse sequence to be applied to a region of interest (ROI) of a subject arranged in the imaging system, where the imaging pulse sequence identifies coil parameters related to at least one coil. The system obtains a first model including a plurality of tissue types and corresponding electromagnetic properties in the ROI. The system then obtains a second model indicating location, orientation, and/or physiological properties of one or more nerve tracks in the ROI. The system estimates a plurality of PNS thresholds in the ROI caused by the imaging pulse sequence applied in the imaging system using the first model, the second model, a nerve membrane model, and the coil parameters.

20 Claims, 18 Drawing Sheets

(51) Int. Cl.
  *A61N 1/08*   (2006.01)
  *A61N 1/05*   (2006.01)
  *A61N 1/36*   (2006.01)
  *A61N 2/02*   (2006.01)
  *A61N 2/00*   (2006.01)
(52) U.S. Cl.
  CPC ............ *A61N 1/3605* (2013.01); *A61N 2/006* (2013.01); *A61N 2/02* (2013.01)
(58) Field of Classification Search
  CPC ............ A61B 5/055–0555; A61B 5/00; G01R 33/20–64
  See application file for complete search history.

(56) References Cited

U.S. PATENT DOCUMENTS

| | | | | |
|---|---|---|---|---|
| 2010/0308829 | A1* | 12/2010 | Vu ........................ | G01R 33/288 324/314 |
| 2011/0040351 | A1* | 2/2011 | Butson ................ | G06F 19/3481 607/59 |
| 2011/0221438 | A1* | 9/2011 | Goodwill ............... | G01R 33/10 324/301 |
| 2011/0306870 | A1* | 12/2011 | Kuhn ................... | A61B 5/0515 600/411 |
| 2013/0079623 | A1* | 3/2013 | Rueckert .............. | A61B 5/0515 600/409 |
| 2014/0354299 | A1* | 12/2014 | Rapoport ............. | G01N 27/023 324/633 |
| 2015/0366523 | A1* | 12/2015 | Ben-Haim ......... | A61K 51/0406 600/431 |
| 2016/0283687 | A1* | 9/2016 | Kamen .............. | A61B 5/04028 |

* cited by examiner

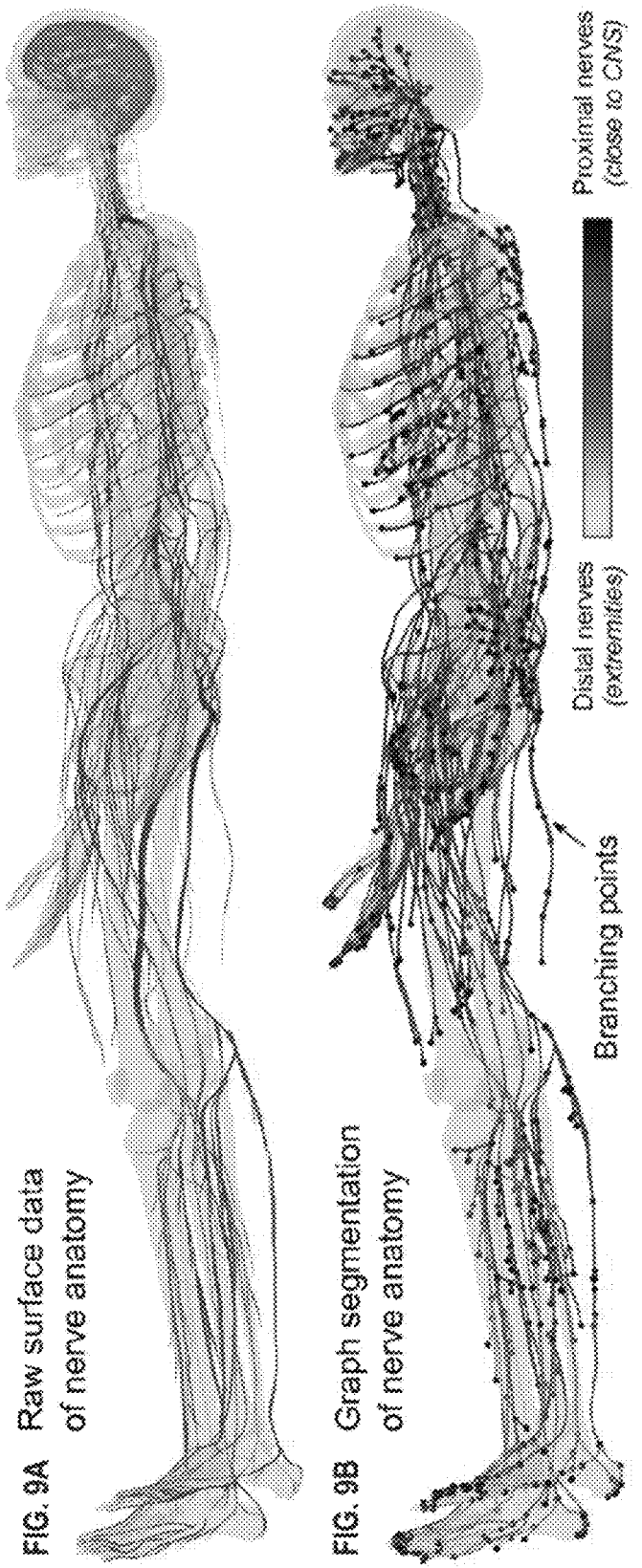

Leg stimulation coil

Arm stimulation coil

Magnetic field strength

Electric field strength

SYSTEM AND METHOD FOR USING CONCOMITANT FIELDS TO CONTROL PERIPHERAL NERVE STIMULATION (PNS) IN MRI IMAGE ENCODING

CROSS REFERENCE

This application is based on, claims priority to, and incorporates herein by reference in its entirety, U.S. Provisional Patent Application Ser. No. 62/420,822, filed on Nov. 11, 2016, and entitled "System and Method for Using Concomittant Fields to Control Peripheral Nerve Stimulation (PNS) In MRI Image Encoding."

STATEMENT REGARDING FEDERALLY SPONSORED RESEARCH

This disclosure was made with government support under R24MH106053 awarded by National Institute of Mental Health, R01EB017337, P41EB015896, K99EB019482, and 4R00EB019482 awarded by National Institutes of Health. The government has certain rights in the disclosure.

BACKGROUND

When a substance, such as human tissue, is subjected to a sufficiently-large, uniform magnetic field (polarizing field $B_0$), the individual magnetic moments of the nuclei in the tissue attempt to align with this polarizing field, but precess about it in random order at their characteristic Larmor frequency. If the substance, or tissue, is subjected to another magnetic field (excitation field $B_1$) that is in the x-y plane and that is near the Larmor frequency, the net aligned moment, $M_z$, may be rotated, or "tipped", into the x-y plane to produce a net transverse magnetic moment $M_{xy}$. A signal is emitted by the excited nuclei or "spins", after the excitation field $B_1$ is terminated, and this signal may be received and processed to form an image.

When utilizing these "MR" signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received MR signals are digitized and processed to reconstruct the image using one of many well-known reconstruction techniques.

Rapid switching of applied magnetic fields in the kilohertz frequency range in the human body induces electric fields powerful enough to cause PNS. PNS has become one of the main constraints on the use of high gradient fields for fast imaging with the latest MRI gradient technology. In recent MRI gradients, the applied fields are powerful enough that PNS limits their application in fast imaging sequences like echo-planar imaging. Application of Magnetic Particle Imaging (MPI) to humans is similarly PNS constrained. Despite its role as a major constraint, PNS considerations are only indirectly incorporated in the coil design process, mainly through using the size of the linear region as a proxy for PNS thresholds or by conducting human experiments after constructing coil prototypes.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 9A shows a human nervous system model as surface data with skeletal system in accordance with an aspect of the present disclosure.

FIG. 9B shows an extracted nerve centerlines color coded by distance from the central nervous system (CNS) in accordance with an aspect of the present disclosure.

DETAILED DESCRIPTION

The disclosure presents for the first time, a framework to simulate PNS thresholds for realistic coil geometries to directly address PNS in the design process. The PNS model consists of an accurate body model for electromagnetic field simulations, an atlas of peripheral nerves, and a neurodynamic model to predict the nerve responses to imposed electric fields. This model can reproduce measured PNS thresholds of leg/arm solenoid coils with good agreement.

Figure 1:
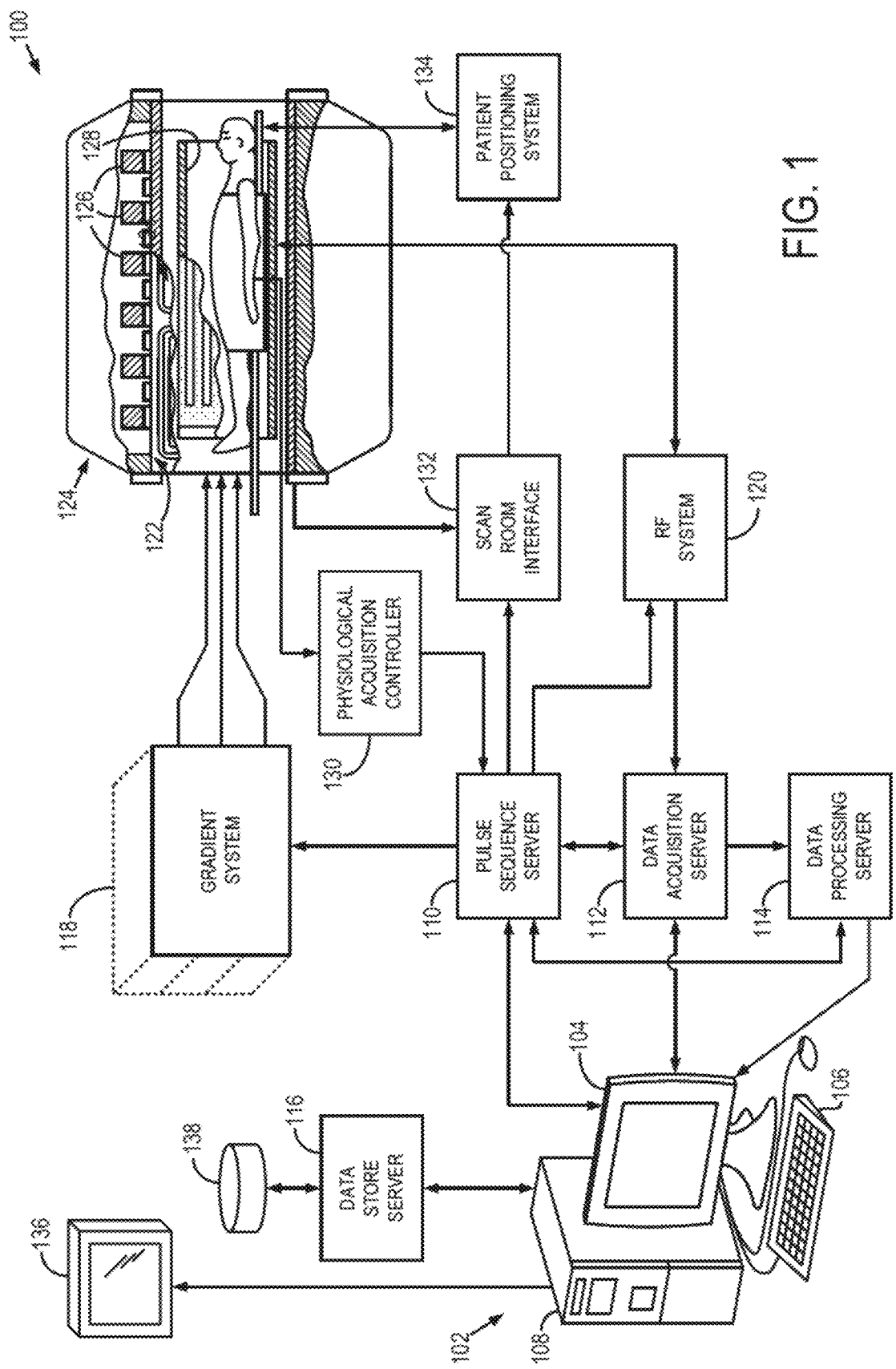
FIG. 1 is a block diagram of an MRI system which employs the present disclosure.

Referring now to FIG. 1, an exemplary MRI system 100 for use when practicing embodiments of the provided method is illustrated. The MRI system 100 includes a workstation 102 having a display 104, a keyboard 106, and computer 108. The workstation 102 provides the operator interface that enables scan prescriptions to be entered into the MRI system 100. The workstation 102 may be coupled to four servers: a pulse sequence server 110; a data acquisition server 112; a data processing server 114, and a data store server 116. The workstation 102 and each server 110, 112, 114 and 116 are connected to communicate with each other.

The pulse sequence server 110 functions in response to instructions downloaded from the workstation 102 to operate a gradient system 118 and a radiofrequency ("RF") system 120. Gradient waveforms necessary to perform the prescribed scan are produced and applied to the gradient system 118, which excites gradient coils in an assembly 122 to produce the magnetic field gradients $G_x$, $G_y$, and $G_z$ used for position encoding MR signals. The gradient coil assembly 122 forms part of a magnet assembly 124 that includes a polarizing magnet 126 and a whole-body RF coil 128.

RF excitation waveforms are applied to the RF coil 128, or a separate local coil, such as a body-matrix phased-array coil (not shown in FIG. 1), by the RF system 120 to perform the prescribed magnetic resonance pulse sequence. Responsive MR signals detected by the RF coil 128, or a separate local coil (not shown in FIG. 1), are received by the RF system 120, amplified, demodulated, filtered, and digitized under direction of commands produced by the pulse sequence server 110. The RF system 120 includes an RF transmitter for producing a wide variety of RF pulses used in MR pulse sequences. The RF transmitter is responsive to the scan prescription and direction from the pulse sequence server 110 to produce RF pulses of the desired frequency, phase, and pulse amplitude waveform. The generated RF pulses may be applied to the whole body RF coil 128 or to one or more local coils or coil arrays (not shown in FIG. 1).

The RF system 120 also includes one or more RF receiver channels. Each RF receiver channel includes an RF amplifier that amplifies the MR signal received by the coil 128 to which it is connected, and a detector that detects and digitizes the I and Q quadrature components of the received MR signal. The magnitude of the received MR signal may thus be determined at any sampled point by the square root of the sum of the squares of the I and Q components M= $\sqrt{I^2+Q^2}$ and the phase of the received MR signal may also be determined $$\varphi = \tan^{-1}\left(\frac{Q}{I}\right).$$

The pulse sequence server 110 also optionally receives patient data from a physiological acquisition controller 130. The controller 130 receives signals from a number of different sensors connected to the patient, such as electrocardiograph (ECG) signals from electrodes, or respiratory signals from a bellows or other respiratory monitoring device. Such signals are typically used by the pulse sequence server 110 to synchronize, or "gate," the performance of the scan with the subject's heart beat or respiration.

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized MR signal samples produced by the RF system 120 are received by the data acquisition server 112. The data acquisition server 112 operates in response to instructions downloaded from the workstation 102 to receive the real-time MR data and provide buffer storage, such that no data is lost by data overrun. In some scans, the data acquisition server 112 does little more than pass the acquired MR data to the data processor server 114. However, in scans that require information derived from acquired MR data to control the further performance of the scan, the data acquisition server 112 is programmed to produce such information and convey it to the pulse sequence server 110. For example, during prescans, MR data is acquired and used to calibrate the pulse sequence performed by the pulse sequence server 110.

The data processing server 114 receives MR data from the data acquisition server 112 and processes it in accordance with instructions downloaded from the workstation 102. Such processing may include, for example: Fourier transformation of raw k-space MR data to produce two or three-dimensional images; the application of filters to a reconstructed image; the performance of a backprojection image reconstruction of acquired MR data; the generation of functional MR images; and the calculation of motion or flow images. Of course, such processing may also be performed on other computer systems that are connected to a network or systems connected to the MRI system 100, such as system 136 described below, or more closely integrated with the MRI system 100.

Images reconstructed by the data processing server 114 are conveyed back to the workstation 102 where they are stored. Real-time images are stored in a data base memory cache (not shown in FIG. 1), from which they may be output to operator display 112 or a display or other connected computer system 136. Batch mode images or selected real time images are stored in a host database on disc storage 138. When such images have been reconstructed and transferred to storage, the data processing server 114 notifies the data store server 116 on the workstation 102. The workstation 102 may be used by an operator to archive the images, produce films, or send the images via a network to other facilities.

PNS during MRI encoding currently limits several aspects of the speed and resolution of MRI methods. Gradient coils with large $G_{max}$ and high slew rates (SR) can be constructed but not used without stimulating the PNS. Since the B field critical to the encoding is accompanied by an electric field, E, and it is this E field that causes PNS, PNS is a fundamental byproduct of fast image encoding. However, the gradient coils used to image encode actually produce fields in each of the three directions, Bx, By, and Bz, and only the Bz component contributes to the image encoding. The other two are commonly referred to as "concomitant fields" or "Maxwell terms" (the latter because their presence is required by Maxwell's equations). These "silent" or "dark" field produce only a minor perturbation on the image encoding.

The present disclosure provides systems and methods to purposefully generate extra concomitant fields. For example, the present disclosure provides systems and methods for using secondary coils that produce mainly these field components. The present disclosure provides systems and methods where, to the extent that these coils can be used in ways that do not perturb image encoding, the coils can be used with an arbitrary current waveform during the image encoding. The fields can be optimized to control or minimize the PNS felt by the patient. Namely, the normal gradient encoding generates an unwanted E field pattern that stimulates the nerves, and the waveform applied to the concomitant field coils attempts to either 1) control or cancel these E fields (and thus reduce or prevent PNS), or 2) reduce the buildup toward the action potential to prevent nerve firing even though E is not completely cancelled. The latter is possible because the nerve firing threshold is known to be perturbed by some temporal features of the B field (and thus E field time course). In normal gradient encoding, it is not generally possible to implement these features because they would degrade the image encoding, but if the B field associated with these coils has no effect on image encoding, these options become possible.

The systems and methods disclosed herein provide systems and methods to overcome one of the fundamental limitations of modern MRI; the limits to gradient strength. The rise of stronger and faster gradients over the last 20 years has caused clinical medicine to come up against the biological limit imposed by PNS. The systems and methods provided herein overcome these limitations.

Figure 2:
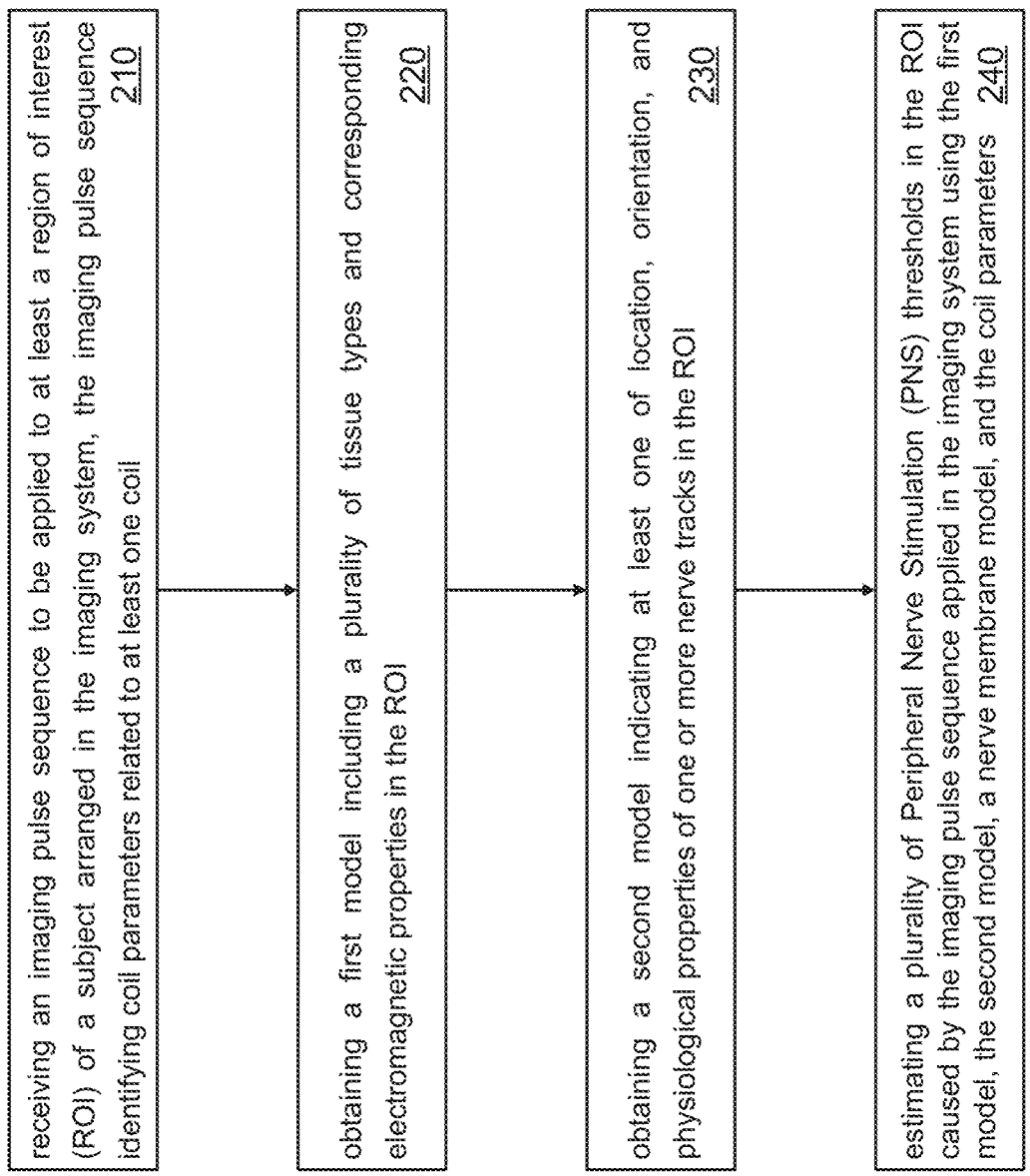
FIG. 2 is an example flow chart setting forth the steps of a method in accordance with the present disclosure.

FIG. 2 is an example flow chart setting forth the steps of a method in accordance with the present disclosure. The method may be implemented in the imaging system as illustrated in FIG. 1.

In step 210, the imaging system receives an imaging pulse sequence to be applied to at least a region of interest (ROI) of a subject arranged in the imaging system, the imaging pulse sequence identifying coil parameters related to at least one coil.

In step 220, the imaging system obtains a first model including a plurality of tissue types and corresponding electromagnetic properties in the ROI. For example, the first model may include a 3D anatomical tetrahedral mesh that models different tissue types and their electromagnetic properties (nerve fibers tracks are meshed with realistic diameter).

In step 230, the imaging system obtains a second model indicating at least one of location, orientation, and physiological properties of one or more nerve tracks in the ROI. For example, the second model may include a nerve fiber atlas that encodes locations, orientations, and physiological properties (such as the degree of myelination, fiber diameter, etc.) of nerve tracks in the human body.

In step 240, the imaging system estimates a plurality of Peripheral Nerve Stimulation (PNS) thresholds in the ROI caused by the imaging pulse sequence applied in the imaging system using the first model, the second model, a nerve membrane model, and the coil parameters. To evaluate the PNS threshold curves, a user may place nerve-sensors at the nerve locations in the realistic body model. The nerve membrane model may combine the Duke model with added nerve-sensors (guided by a human anatomy database).

In some embodiments, a nerve-sensor may include a myelinated nerve with equally spaced nodes of Ranvier (spacing between 0.5 mm and 1.5 mm, depending on the fiber diameter). The nerve-sensor is used to monitor the nerve membrane dynamics, which may include possible action potentials (AP), using a detailed numerical model of nerve fibers. Thus, the E-fields may be modulated in both amplitude and frequency (0.5 to 50 kHz) until generation of an AP to generate PNS threshold curves. For an MPI gradient coil, the amplitude may be modulated between 0 mT to 100 mT and the frequency may be modulated between 10 kHz to 200 kHz. For an MRI gradient coil, the amplitude range may be determined by a hardware threshold of the magnetic resonance imaging (MRI) scanner and the frequency range is 0.1 kHz to 5 kHz for a MRI gradient coil. Here, in the MRI scanner, the magnetic field may be a gradient that changes across the body. When the current in the coil increases, the applied gradient, G, gets bigger. Thus, say delta G of the waveform causes PNS. The hardware threshold may be the biggest delta G allowed by the hardware of the MRI scanner, which may be as big as 300 mT/m, but more typically, around 80 mT/m.

Figure 3A:
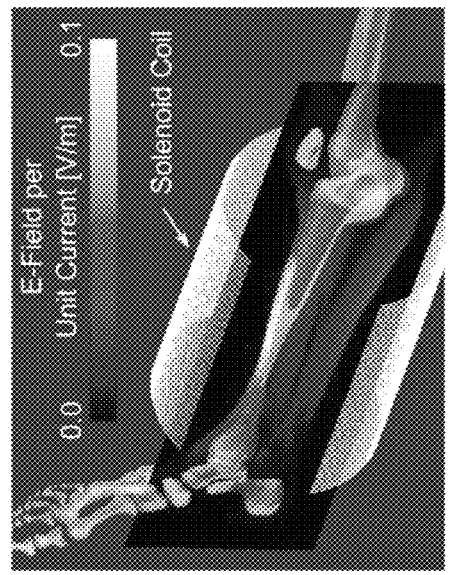
FIG. 3A is an example experiment setup in accordance with the present disclosure.

FIG. 3A is an example experiment setup in accordance with the present disclosure. The experimental setup may be used for measurement of the leg stimulation threshold curves.

Figure 3B:
FIG. 3B is an example simulation setup in accordance with the present disclosure.

FIG. 3B is an example simulation setup in accordance with the present disclosure. The simulation setup may adopt a modified Duke model to simulate the leg stimulation thresholds. In both FIG. 3A and FIG. 3B, the solenoid coil is illustrated. However, other coils may be used or simulated in other examples.

Figure 4:
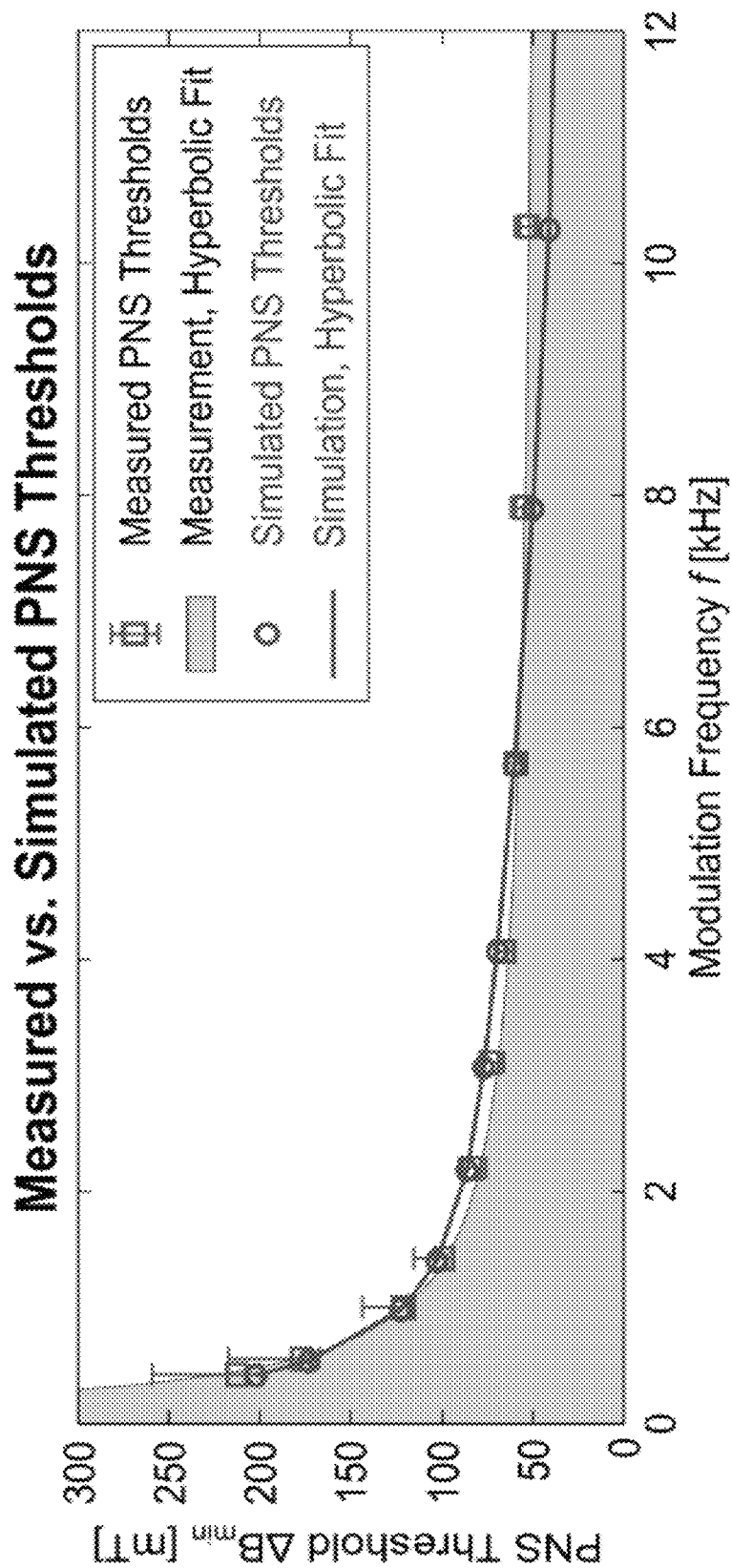
FIG. 4 shows measured and simulated PNS threshold curves in accordance with an aspect of the present disclosure.

FIG. 4 shows measured and simulated PNS threshold curves in accordance with an aspect of the present disclosure. The measured PNS threshold curve is illustrated by a small square with a grey curve while the simulated PNS threshold curve is illustrated by a small circle with a red curve. Here, the simulated PNS threshold curves in the leg belongs to the worst case nerve-sensor. $\Delta B_{min}$ may indicate the minimum B-field created by the MPI coil that generates an AP at a given modulation frequency. In FIG. 4, there is good overall agreement between the simulated and measured data.

Figure 5:
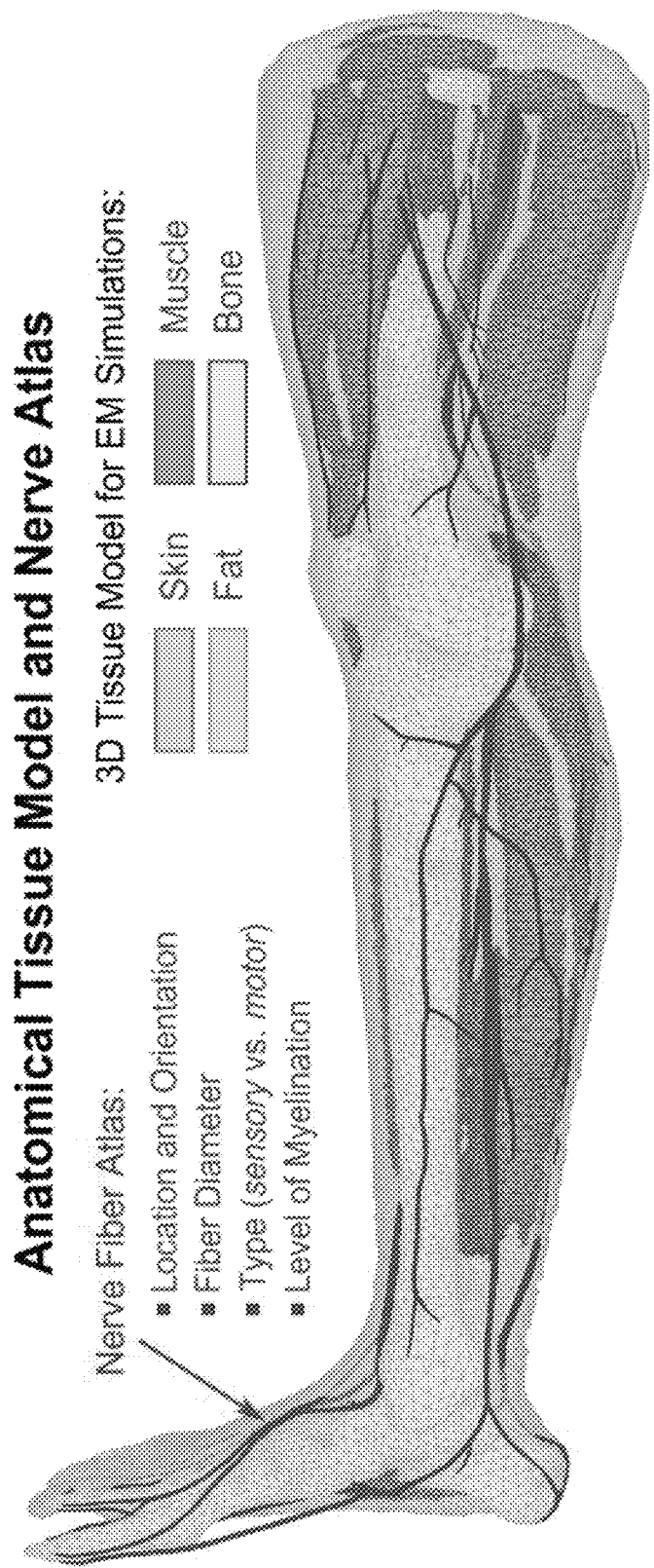
FIG. 5 shows an anatomical model overlaid with the nerve atlas in accordance with an aspect of the present disclosure.

FIG. 5 shows an anatomical model overlaid with the nerve atlas in accordance with an aspect of the present disclosure. The different tissues are color coded. The nerve atlas is overlaid on the anatomical model, where nerve atlas encodes physiological properties and locations of the nerves.

Figure 6:
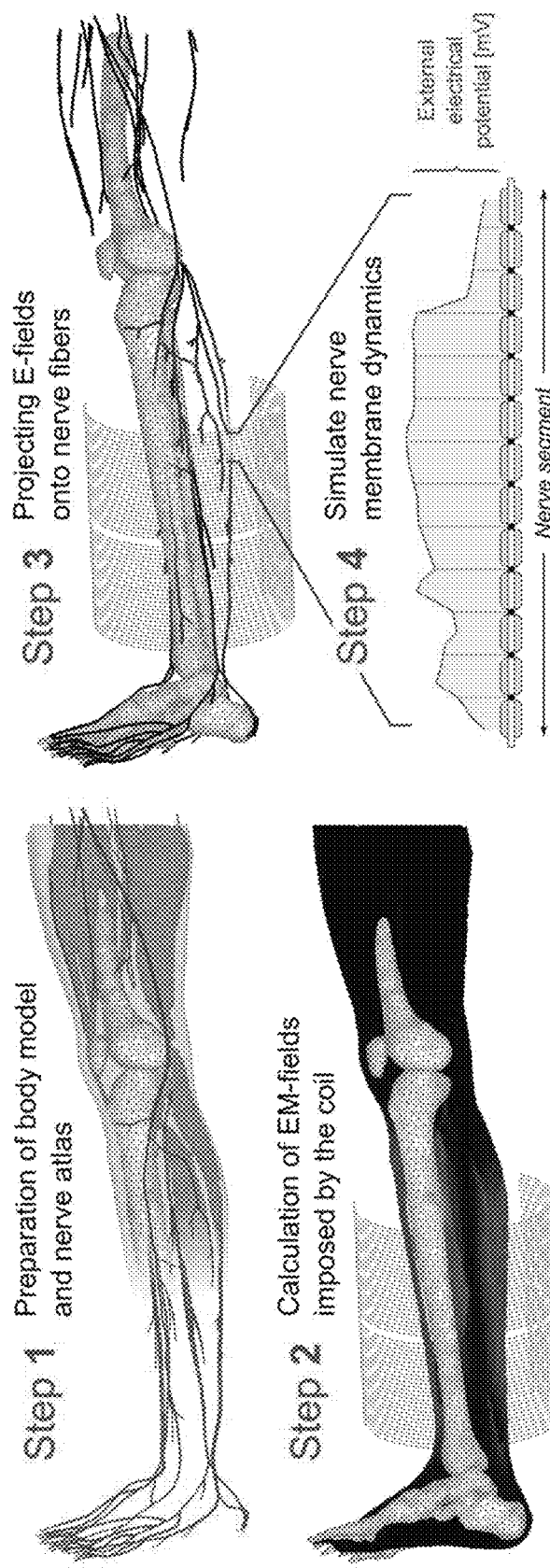
FIG. 6 shows an example flowchart of the PNS simulation process in accordance with an aspect of the present disclosure.

FIG. 6 shows an example flowchart of the PNS simulation process in accordance with an aspect of the present disclosure. In order to model PNS in the body induced by the switching of electromagnetic fields created by an external coil, an example workflow is shown in FIG. 1. The example workflow includes three main components:

(A) a surface-based whole body tissue model used for calculation of the internal electromagnetic (EM) fields, (B) a detailed atlas of the nerve fibers in the human body embedded in the same anatomical model, and (C) a numerical framework to model the nerve dynamics in presence of external E-fields.

The gradient design system may include a computer system that performs the following steps to generate the PNS threshold curves for a given coil geometry:

In step 1, the computer system may preprocess the surface body model to be compatible with finite element EM field simulations and prepare the nerve atlas to be compatible with the neurodynamic model. In some embodiments, this preprocessing step is only required once and can be reused for the analysis of multiple coil geometries. If an individual surface body model is desired, the preprocessing step may be adapted accordingly.

In step 2, the computer system may simulate the magnetic and electric fields in the body model generated from a time-varying current applied to the coil using an EM field simulation platform. For example, a commercial EM field simulation platform such as CST (Darmstadt, Germany) may be adopted.

In step 3, the computer system may superimpose the atlas of human peripheral nerve fibers on the fields. For example, the simulated electric fields are projected onto the nerves and integrated to obtain the effective electric potential along the fiber. This provides the relevant electric entity that can lead to action potential generation and is used as an input to the neurodynamic model.

In step 4, the computer system may evaluate the neurodynamic model by providing the response of the nerve fiber to the external electric potentials. The nerve fiber model returns the internal membrane potentials. Here, an action potential (AP) is recognized as a sudden membrane depolarization in response to a small increase in the applied fields.

Figure 7:
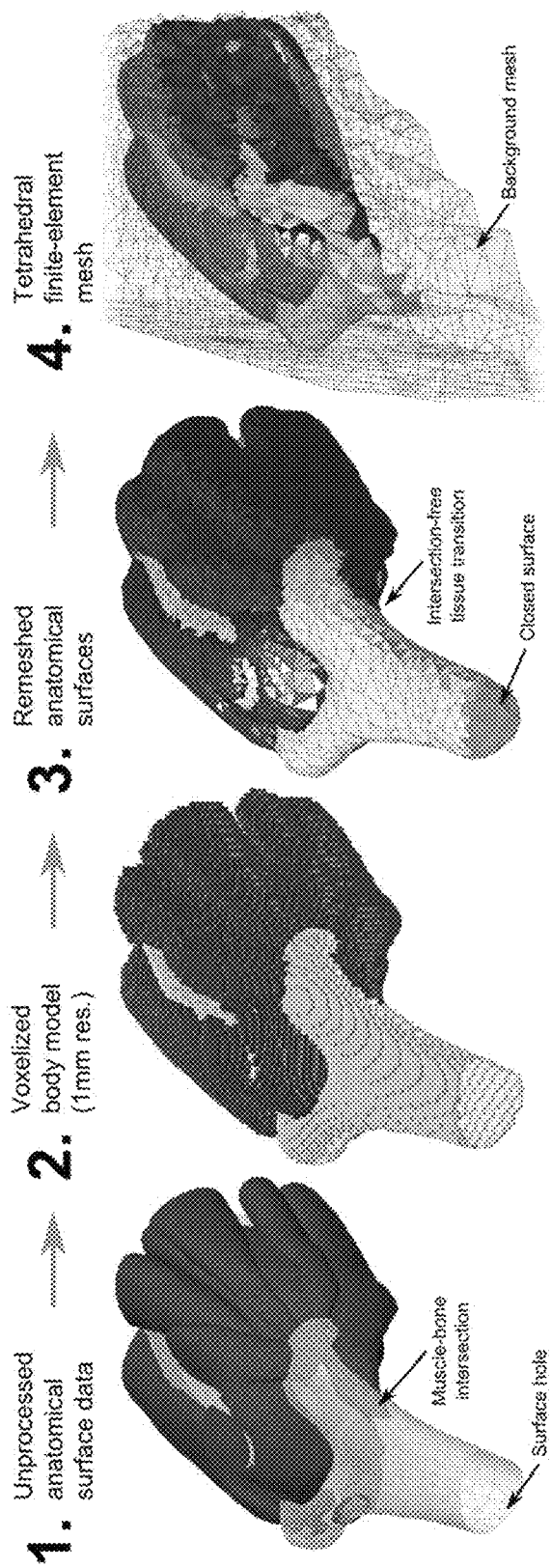
FIG. 7 shows an example processing pipeline of a body model region in accordance with an aspect of the present disclosure.

FIG. 7 shows an example processing pipeline of a body model region in accordance with an aspect of the present disclosure. Here, the body model region may be an elbow region including muscle, bone, and articular capsule. The example processing pipeline of the exemplary body model region may start from:

(1) obtaining unprocessed anatomical surface data, which may be provided by Zygote, (2) discretizing (voxel) body model with 1 mm voxel size, (3) obtaining watertight intersection-free surfaces via segmentation of the voxel model, and (4) computing cross section of an exemplary tetrahedral mesh using CGAL, similar to the mesh generated by CST Microwave Studio for finite-element EM field simulations.

In one or more embodiments, the realistic body model may be based on the anatomical surface data developed by Zygote (American Fork, Utah, USA). The Zygote anatomical data includes 12 different tissue classes: skeleton, muscular system, respiratory system, digestive system, nervous system, circulatory system, connective tissue, integumentary system, lymphatic system, urinary system, and endocrine system. Each tissue class is described by a single surface mesh. Since the Zygote model was initially developed for teaching and visualization purposes, further processing may be required in order to guarantee that it can be used in conjunction with electromagnetic simulation platforms.

For example, the input surface mesh to the EM simulation platform (CST AG, Darmstadt Germany) requires an orientable 2-manifold mesh without self-intersections and without intersections of the different tissue classes. To achieve this, the imaging system may first discretize the surface mesh data to obtain a voxel model at 1 mm isotropic resolution for each tissue class (FIG. 6, Step 1 and 2). The voxels of all tissue classes were combined into a single voxel model. Skin tissue voxels were added by performing a morphological dilation algorithm of the outer body hull, assuming a skin thickness of approx. 3 mm (i.e., 3 voxels). Every interior voxel that was not assigned to any of the tissue classes at this point may be defined as fatty tissue. Note that this assumption yields distributions of fatty tissue very similar to well-established body models like the Virtual Population 3.0. This voxelized model guarantees a single label per voxel.

In this disclosure, the imaging system may perform a multi-domain surface segmentation of the 1 mm voxel model using the Computational Geometry Algorithms Library (CGAL). The output surface mesh of the segmentation generates a non-intersecting closed surface mesh for each tissue class where all neighboring tissues align perfectly (FIG. 6, Step 3), i.e., neighboring tissues share the exact same faces without creating empty regions or overlaps. However, the resulting surface meshes do not necessarily establish 2-manifold geometries. In the context of surface triangulations, this means that every edge of a mesh is used by exactly 2 faces. Physically, 0-manifold or 1-manifold features of a mesh correspond to physical structures that become infinitely thin or small. Therefore, it may be necessary to remove these invalid features from the surface mesh.

For that purpose, the imaging system may implement a method to repair any existing surface mesh error and thus prepare the surface meshes for usage in our EM field simulations. This pre-processing includes elimination of 0-manifold and 1-manifold features, removal of excessively small faces/structures and low-quality faces (i.e., very long and thin faces). In short, this surface mesh repair routine first deletes the faces that correspond to a mesh error. Usually this deletion creates holes in one or more of the tissue surfaces. The routine then identifies possible face configurations to close these holes without causing new surface mesh errors or empty regions. The process is repeated until all surface errors are repaired.

An important advantage of this approach over commonly used mesh repair tools is that all tissue surfaces are processed simultaneously in order to ensure that a correction step that is applied to one tissue surface does not introduce intersections or errors in any neighboring tissue surface. Although the creation of the surface body model is computationally intensive (even starting with a commercial meshed model), it only has to be done once per body model. The different tissues were assigned electromagnetic properties (conductivity and permittivity) using the frequency-dependent Gabriel database. Note that the permittivity increases dramatically as frequency becomes very low, and our simulations reflect this.

Figure 8:
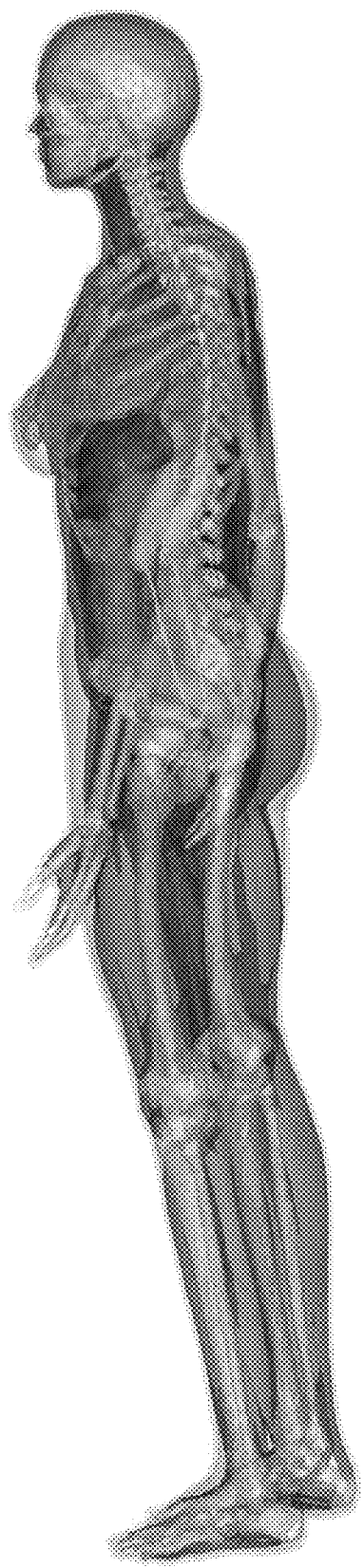
FIG. 8 shows a surface-based whole body model used for the simulation of the EM fields in accordance with an aspect of the present disclosure.

FIG. 8 shows a surface-based whole body model used for the simulation of the EM fields in accordance with an aspect of the present disclosure. Here, the final surface body model may be used in an EM field simulation environment (such as CST) in order to generate a tetrahedral finite-element mesh for calculation of the EM fields (an exemplary finite element mesh is shown in Step 4 of FIG. 6).

The nerve atlas may be Zygote anatomical model or any other model including detailed atlas of the peripheral nerves or other nerves in the ROI. Here, like the organ surface mesh data in the model, some processing may be needed to use this nerve atlas information in conjunction with the PNS membrane dynamics model.

FIG. 9A shows a human nervous system model as surface data with skeletal system in accordance with an aspect of the present disclosure.

FIG. 9B shows an extracted nerve centerlines color coded by distance from the central nervous system (CNS) in accordance with an aspect of the present disclosure.

For example, from the original Zygote nerve atlas illustrated in FIG. 9A, the imaging system may extract paths of the peripheral nerve bundles as 3D curves with labels at their three types of phylogenic points; starting point, end-point, and any branching point as shown in FIGS. 9A and 9B. The starting point of the peripheral nerve fibers was the CNS, most frequently the spinal cord and the end-point was typically a distal extremity.

In the disclosure, the term "nerve tracks" may be defined as individual nerve bundle segments between any of the phylogenic points identified in the previous step. The model contains approximately 1600 nerve tracks. The nerve tracks between the phylogenic points are represented in 3D by centerline curves that follow the center of the surface mesh of each nerve track.

For example, this may be achieved by first applying a so-called geodesic algorithm that computes the shortest path along the edges of the surface mesh that connects the two phylogenic points. The resulting 3D curve runs along the surface of the mesh (i.e., on the surface of the "nerve tube"). In order to obtain the nerve centerline from this (i.e., the curve running along the center of the "nerve tube"), the imaging system may first voxelize the entire nerve tree at 0.1 mm resolution and compute the distance measure of this voxelized nerve tree. The distance measure specifies, for each voxel, the distance to the nearest surface of the nerve tracks. Note that the distance measure is greatest for the center points of the nerve tube. The centerline curve may be generated from these center points.

Finally, the imaging system may fit the resulting 3D curve with free-knots B-spline to avoid excessively high (unrealistic) curvatures of the nerve tracks. The final nerve atlas after this processing is shown in FIG. 9B, which has been color-coded by the number of branch points between the nerve track and the CNS.

Figure 10A:
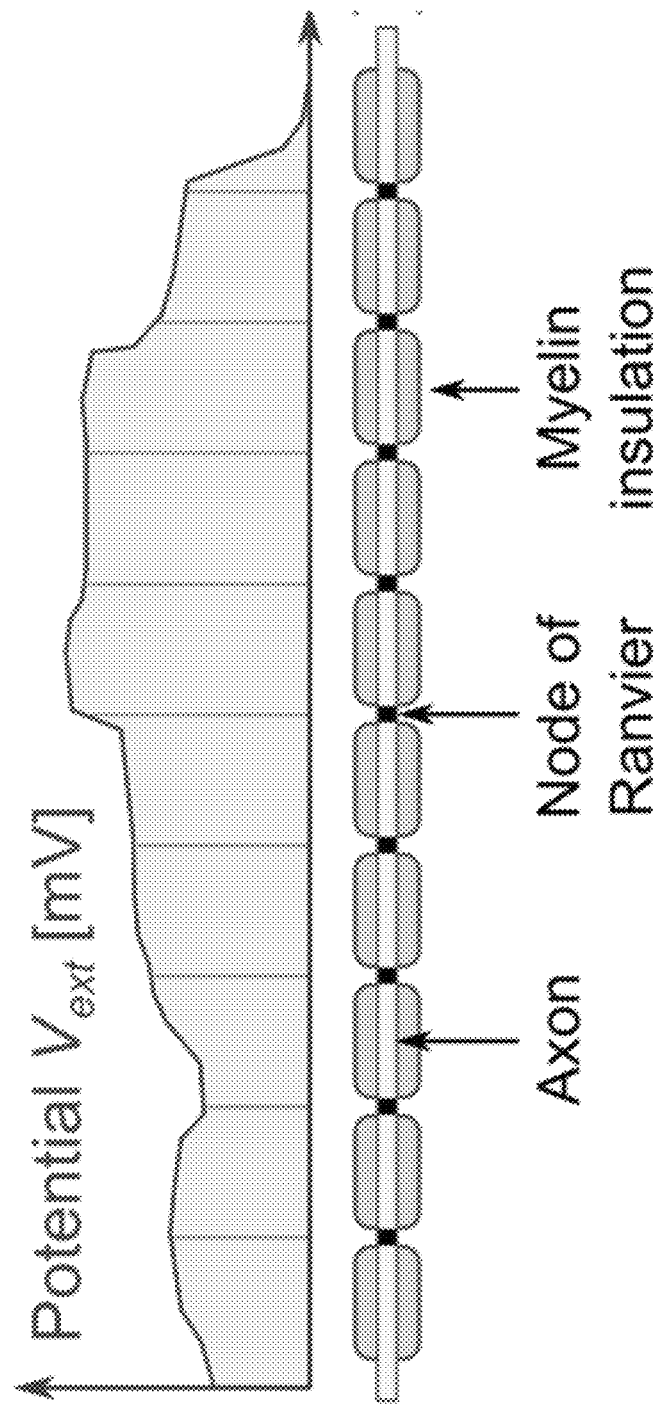
FIG. 10A shows schematic of the discretization of the potential Vext along the nerve segment with respect to the nodes of Ranvier.

FIG. 10A shows schematic of the discretization of the potential Vext along the nerve segment with respect to the nodes of Ranvier. Here, Vext may be determined from integrating the induced electric field calculated in Step 2 of FIG. 6. Node spacing may be assigned based on estimated fiber diameter.

Figure 10B:
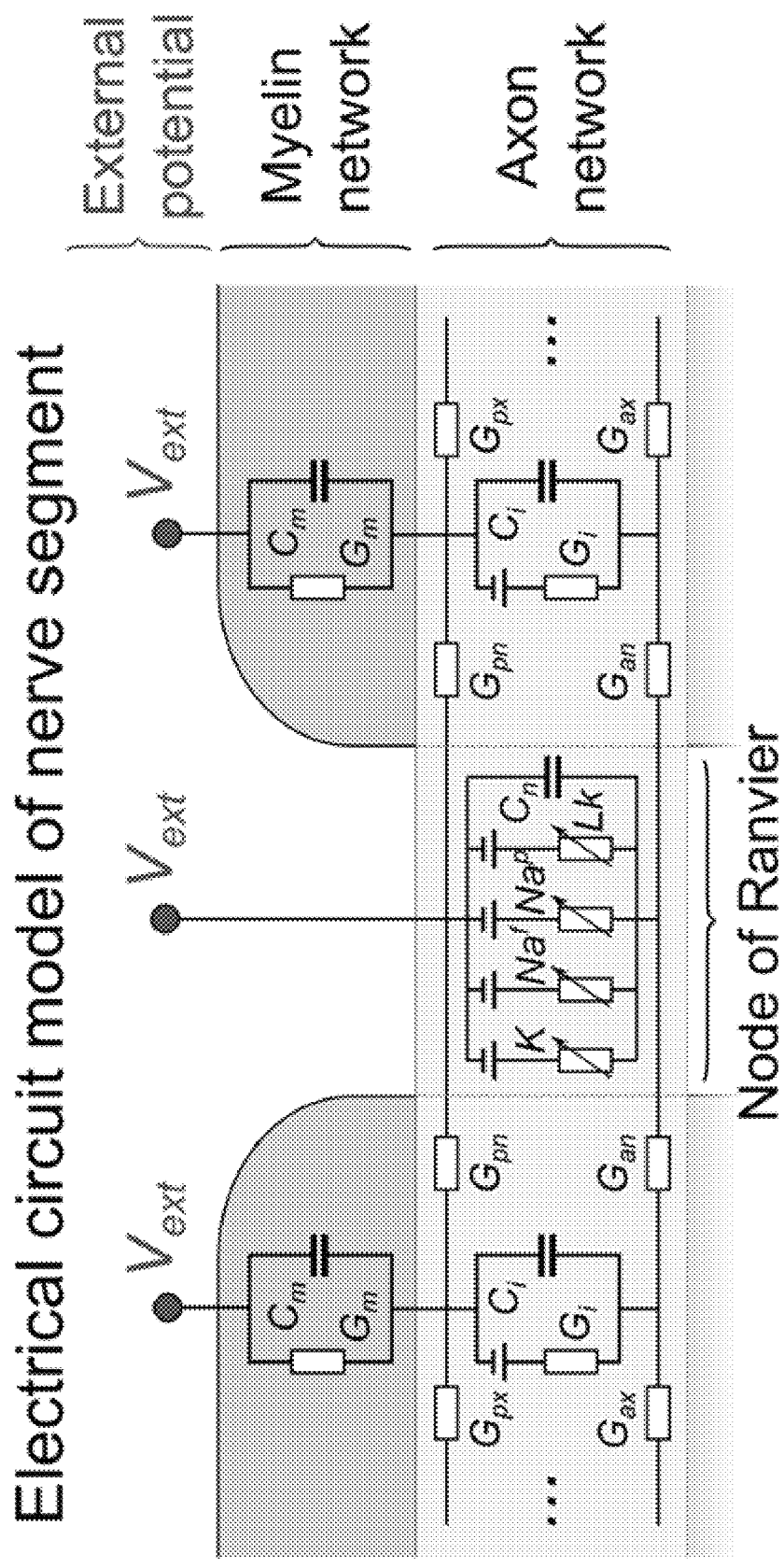
FIG. 10B shows an electrical equivalent circuit for the MRG nerve model on each side of a node of Ranvier.

FIG. 10B shows an electrical equivalent circuit for the MRG nerve model on each side of a node of Ranvier. Here, action potentials are created when the transmembrane potential change becomes greater than approximately 20 mV.

In some embodiments, the electric fields calculated in the body model may be projected onto the nerve fiber path and integrated to obtain potential differences along the fibers. These spatially varying potentials Vext are modulated by the driving waveform of the coil and fed into the circuit model with myelin and node of Ranvier parameters. For example, the McIntyre-Richardson-Grill model (MRG) may used to simulate the response of the nerve to the voltage potentials induced along the fiber by the external fields. The MRG electrical nerve model is based on a double-cable representation of the myelinated axons (the inner cable models the axon, the outer cable models the myelin insulation sheath). Electrically speaking, these cables are connected in parallel, as shown in FIG. 10B.

In the above example, the MRG model is used because it explicitly models action potential (AP) initiation. The effect of the local myelin insulation sheath on the excitability of the nerve is explicitly included, making this model more appropriate for simulation of PNS, since peripheral nerves are heavily myelinated. Since the myelin sheath insulates the axon, the nerve is most sensitive to the induced electric field at the locations of the nodes of Ranvier where the axon is in direct contact with the extra-cellular space. Each of the three nerve compartments (axon, myelin, and node of Ranvier) is modeled by RC-circuits with capacitance and resistance properties specific to each compartment (for the exact electrical parameters). However, other models may be used as well.

In order to be able to simulate action potential initiation, the RC-circuit model of the nodes of Ranvier compartments includes non-linear terms, implemented as voltage-dependent resistances that model the sodium and potassium ion channels. This means that once the nerve fiber is strongly depolarized, the membrane becomes permeable for sodium and potassium ions (in the electric model this is represented as a small resistance), which leads to a large current flowing through the membrane and thus to an action potential. The different RC-circuits are connected via conductances that specify the transaxial and axial conductivity of the nerve. This allows modeling of the propagation of action potentials along the nerve fiber at realistic conduction velocities (approximately 25 m/s to more than 100 m/s, depending on the axon diameter).

For example, the MRG electrical circuit shown in FIG. 10B may be mathematically represented as a set of coupled differential equations. The input to the model is the external electric potential changes Vext imposed by the external coil. The imaging system may compute these potentials using electromagnetic simulation and by interpolation of the resulting electric fields along the nerve fiber paths. The output of the model is the resulting transmembrane potential change over time at each compartment of the nerve fiber model. These transmembrane potential changes are analyzed to decide whether or not an action potential has been initiated.

In one or more embodiments, the imaging system may tag each track of the nerve atlas with information about local nerve fiber diameters from a local or remote database. These fiber diameters may be used to feed the correct parameters into the MRG nerve membrane model. For example, the model parameters of the MRG model may vary with axon diameter for 9 different diameters (ranging from 5.7 μm to 16.0 μm). This includes the thickness of the myelin insulation sheath that increases with fiber diameter. Stated conversely, the conductance of the myelin compartment decreases with fiber diameter. The spacing of the nodes of Ranvier also increases with the fiber diameter, from 0.5 mm for a 5.7 μm fiber to 1.5 mm for a 16.0 μm fiber. Together, the increase in both the myelin sheath thickness and node of Ranvier spacing with nerve diameter result in much higher excitability for large diameter fibers compared to smaller ones.

Additionally or alternatively, fixed parameters (non-varying with diameter) may also be used. To provide a full set of membrane model parameters for each nerve track in our nerve tree, the imaging system may assign nerve diameters based on the type of nerve fibers present in the nerve track. If any motor nerve fibers are present, the imaging system may assume large fiber diameters of 16 μm. For nerve tracks that only consist of sensory nerves (e.g., the digital nerve branches in the fingers, the sural nerve in the calf, or the posterior cutaneous nerve in the shoulder), smaller nerve fiber diameters (10 μm) may be assigned. Autonomous nerve bundles (e.g., those controlling the digestive or cardiovascular system) usually contain very small fibers (in the order of 2 μm diameter). The imaging system may refine the nerve fiber properties of the nerve atlas, as more detailed information becomes available (e.g., via studies of nerve conduction velocities that can be correlated with the fiber diameter).

Figure 11:
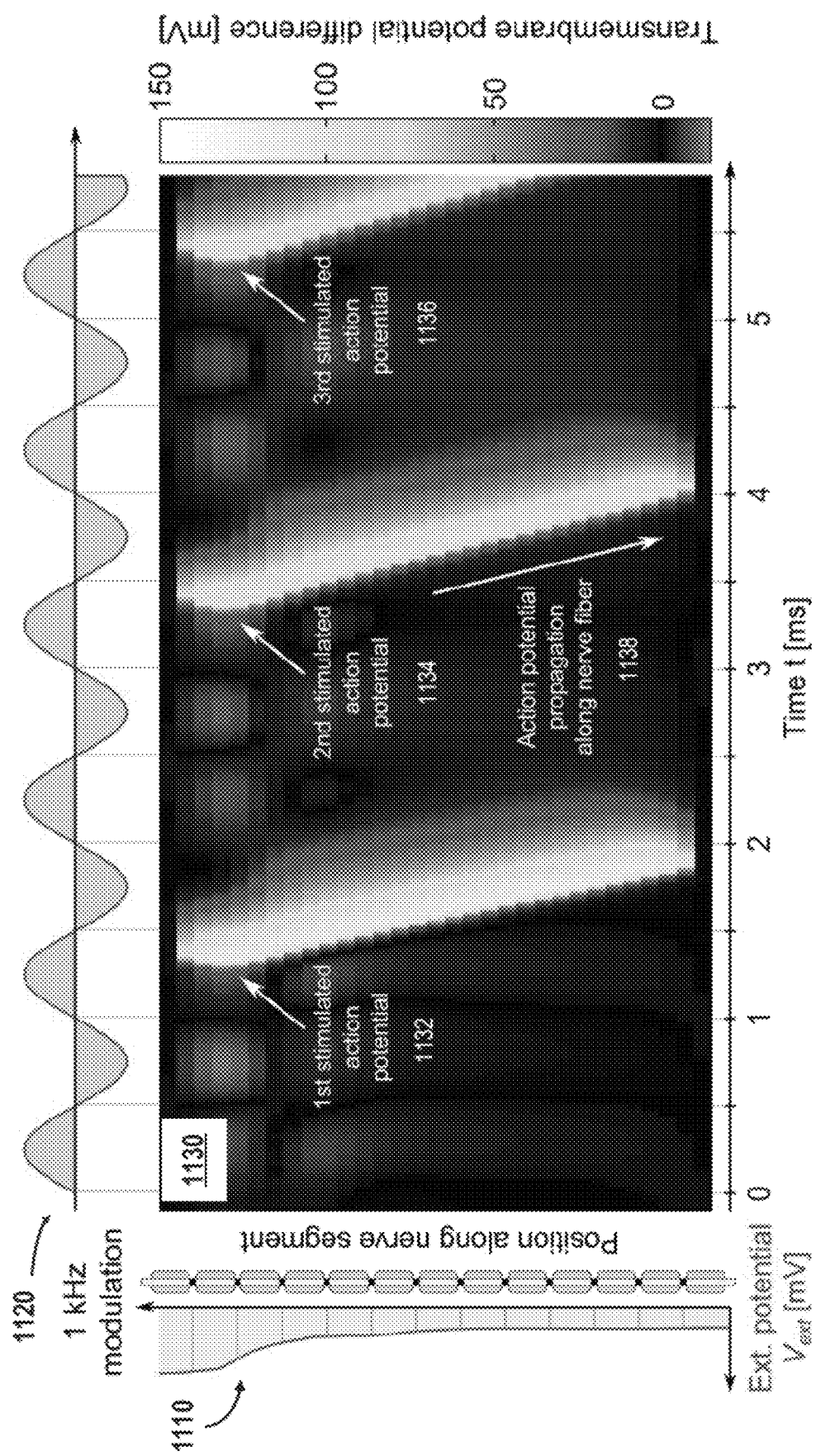
FIG. 11 shows an example evaluation of the nerve membrane model in accordance with an aspect of the present disclosure.

FIG. 11 shows an example evaluation of the nerve membrane model in accordance with an aspect of the present disclosure. The PNS threshold may be defined as the smallest external field modulation strength that initiates an action potential. The PNS threshold depends on the frequency of the external electromagnetic excitation, the coil geometry, and the subject's anatomy, which modulates both the strength of the electric field and its orientation with respect to the nerve fiber. To compute the PNS threshold curve, the imaging system may modulate the spatial map of electric potentials (output of the electromagnetic simulation) interpolated along the nerve fiber by a sinusoidal waveform of different frequencies ramping the amplitude up for each frequency. The imaging system then records the amplitude $B_{min}$ that initiated an AP.

FIG. 11 illustrates an example titration process. In 1110, the potential created by coil along the nerve segment (Vext) is illustrated. In 1120, the time modulation of Vext (1 kHz sinusoid at 125% of the PNS threshold) is illustrated. In 1130, the transmembrane potential as a function of space (position along the nerve, vertical axis) and time (horizontal axis) are shown with the creation of an action potential which then travels with a fixed velocity in space. In 1130, the first stimulated action potential 1132, the second stimulated action potential 1134, and the third stimulated action potential 1136 are almost equally separated in time. The arrow 1138 also shows the action potential 1134 may propagate along the nerve fiber.

FIG. 11 shows the time evolution of the membrane potential for a 16 μm fiber diameter in response to an applied external waveform. The curve 1110 shows the external electric potential imposed by the coil at the different nodes of Ranvier. This spatially varying electric potential pattern is modulated in time by the 1 kHz sinusoidal waveform 1120. The resulting membrane dynamics are shown in 1130. In this 2D plot, the vertical axis specifies the spatial location along the nerve segment and the horizontal axis specifies time. During the first two sinusoidal half-lobes, the nerve segment is alternatively hyperpolarized (green) and depolarized (red) but only the third half-lobe initiates an action potential (yellow) in the upper part of the segment. This action potential then propagates along the nerve segment without significant further perturbation by the external electric potential's waveform. After this first action potential the nerve membrane recovers (this is the refractory period during which the ion-channel pumps are active and no action potential can be evoked) and a second and third action potential are initiated by the 7th and 11th sinusoidal half-lobe, respectively.

Figures 12A, 12B:
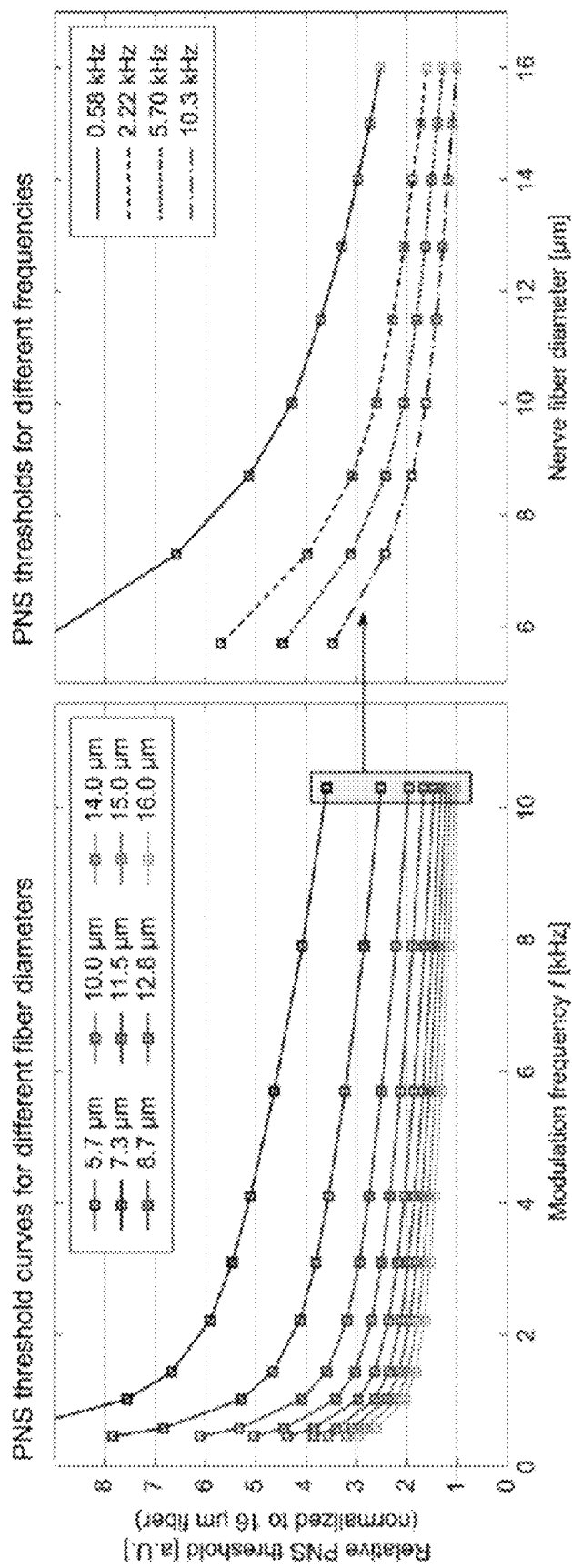
FIG. 12A shows a PNS thresholds as a function of the frequency of the applied coil current (sinusoidal current) for different fiber diameters in accordance with an aspect of the present disclosure.
FIG. 12B shows a PNS thresholds as a function of fiber diameter in accordance with an aspect of the present disclosure.

FIG. 12A shows a PNS thresholds as a function of the frequency of the applied coil current (sinusoidal current) for different fiber diameters in accordance with an aspect of the present disclosure. FIG. 12A shows PNS threshold curves for a nerve segment in the leg for varying values of the fiber diameter (5.7 μm to 16.0 μm). The field modulation strength (vertical-axis) is normalized to the PNS threshold for the largest fiber (16.0 μm diameter) at the 10.4 kHz modulation frequency. These PNS threshold curves coincide with experimental observations and theoretical predictions that nerve fibers with a large diameter are more easily excited than smaller fibers. The threshold for the smallest diameter fiber is about 3.5 fold that of the largest fiber simulated (16.0 μm).

FIG. 12B shows a PNS thresholds as a function of fiber diameter in accordance with an aspect of the present disclosure. FIG. 12B shows PNS thresholds as a function of fiber diameter, for given constant frequencies of the applied fields. Note that the PNS thresholds change very quickly for small fiber diameters and rather slowly for large fibers.

For the leg coil, approximately 8.6 meters of nerve fibers need to be analyzed (resulting in approximately 5700 nodes of Ranvier and 63000 electrical compartments). For the arm simulation, there are 10.3 meters of nerve fibers resulting in 6900 nodes of Ranvier and 75900 electrical compartments. When solving the underlying differential equation, the imaging system may use a time step of 0.5 μs for a 1 kHz coil current waveform and decreased this value linearly for higher frequencies (i.e., independently from the frequency every bipolar pulse is resolved by 2000 time points). Thus, a smaller time step was used compared to other nerve model simulations. A time step of 1 to 5 μs may be used to accurately solve the differential equation of the MRG neurodynamic model.

In some embodiments, a smaller time-step was needed. This difference may be derived from a more conservative convergence criterion or reflects a more complicated temporal dynamics within the nerve model. The stimulus consisted of 15 sinusoidal periods, resulting in durations of 32.6 ms to 1.5 ms for coil current frequencies of 0.46 kHz to 10.3 kHz. Note that based on these parameters, calculation of PNS threshold curves using the entire nerve tree would require at least a week of computation time (assuming that no parallelization is used).

Processing the entire nerve tree may result in a high computational overhead. For example, if a nerve track branches into a major track and a minor track, the part of the nerve prior to the branching point will be simulated twice: once as being part of the major track and once as being part of the minor track (unless the nerve track is divided appropriately).

To increase computational efficiency, the nerve tree may be divided into smaller sub-segments without any branches, where each sub-segment has a reasonable length (ideally less than 100 nodes of Ranvier). These sub-segments of the nerve tree may be referred as nerve segments. Dividing the nerve tree into smaller nerve segments also means dividing the underlying differential equation, which may cause numerical instabilities and artefacts at the boundaries of the nerve segments. Therefore, we implemented methods to identify the locations of the nerve tree, where dividing the nerve fiber into multiple nerve segments only has a mild effect on the model accuracy and, therefore, on the resulting PNS thresholds. Note that the second spatial derivative of the extracellular potential along the fiber can be considered the main determinant (also referred to as "activation function") of nerve stimulation. This metric is often used to guide the development of electromagnetic coils for neuro-stimulation or neuro-modulation devices.

As a consequence, an electric potential pattern that varies only linear along the fiber does not generate an activation function (no stimulation of the nerve). Instead the electric potential leads to a constant current flow along the fiber without any current flowing through the membrane. This means that the external electric field is not effective at depolarizing the membrane and the nerve segment may not initiate an action potential in this region. Thus, these regions can be safely ignored when searching for the PNS threshold.

Dividing the nerve tree into nerve segments at these locations only has negligible effects on the excitability of the nerves and, therefore, on the AP thresholds. After defining the nerve segments, the imaging system may further reduce computation time by solving the MRG model only for those segments where the electric potential leads to a substantial flow of current through the membrane (possibly leading to an AP). Note that the definition of individual nerve segments also allows for a heavy computational parallelization since every nerve segment can be excited and simulated independently. In one example, the nerve model are simplified to 304 and 359 nerve segments for the leg and arm stimulations, respectively.

In one or more embodiments, the nerve segments are particularly sensitive to spatial deformations that alter the curvature of the segments (e.g., only applying shifts to a nerve segment within a linearly varying electric potential does not influence the stimulation threshold). In order to implement a spatial uncertainty of the nerve segments path, the imaging system may define a tube of a certain radius (2 mm and 4 mm) following the nerve segment and allowed the nerve to traverse the tube along a flexible path. This is achieved by using a 3D Gaussian deformation field: for each spatial dimension 10 three-dimensional Gaussians are randomly distributed within the bounding box of the nerve segments (overall 30 Gaussians). The standard deviation of the Gaussians (2 cm in this example) determines the smoothness of the deformation; the function value of the sum of Gaussians determines the local deformation strength along the different axes. The weighting of the 30 Gaussians was chosen randomly such that 1) the deformed nerve segment remains within the tube (this limits the maximum local deformation), and 2) the segment does not intersect the bone tissue or outer hull of the body (for example for superficial nerve segments).

In one example, the imaging system may generate 20 deformed nerve segments for tube radii of 2 mm and 4 mm and computed PNS threshold curves for each segment. The imaging system may then use the standard deviation of the PNS thresholds over the 20 segments as means of the sensitivity of the predicted threshold curves to the path of the nerve segment.

Here, the simulated PNS threshold curves are compared with those measured experimentally using leg and arm solenoid coils applied to healthy volunteers. The two coils were simulated based on their described dimensions and geometry using CST's frequency domain solver which uses a low-frequency approximation of Maxwell's equations. The coils were modeled using infinitely thin, perfect electrical conductor current paths. Boundaries were modeled as a box of perfect electrical conductors (PEC) enclosing the entire simulation domain 50 cm away from the tissue model or the coil (low-frequency FEM solvers usually require PEC boundary constraints).

It has been found that this PEC boundary spacing is reasonable for these two simulation setups and that increasing the boundary spacing to 500 cm altered the tissue electric field maps by only about 1-2%. The experimental comparison data was taken in an open setting (approximately "free space"). However, MRI gradients are used within the more complex conducting environment of the magnet and its cryostat, which might need to be taken into account for MRI gradient studies. The simulated leg coil consisted of 54 turns in a single layer (length of 24 cm, diameter of 19 cm); the arm coil consisted of 72 turns in two layers (length of 17 cm, diameter of 11 cm). The body model was placed inside the coils to mimic the experimental setup as closely as possible, although only the photo in the published paper provided guiding information.

In the simulations, only the leg (until 30 cm above the hip joint) and the arm (including the shoulder joint) were simulated as the effects of the coils are limited to these regions.

MRI gradient encoding most often uses trapezoidal waveforms where electric field generation is confined to well-defined pulses during the ramps of the trapezoid. It is well documented that for a given peak B-field strength, the trapezoidal waveform has increased PNS thresholds compared to a sinusoidal waveform. Furthermore, it has been observed that the PNS thresholds increase linearly with the pulse duration (ramp rise-time). In order to determine if our model captures these two observations, both sinusoidal and trapezoidal waveforms are applied using ramp rise times relevant to MRI (from 0.1 to 1.0 ms). The PNS thresholds (applied solenoid B-field amplitude) as a function of pulse duration were assessed in terms of linearity with a linear fit and in terms of the chronaxie times (i.e., the slope of the linear fit).

Figure 13A:
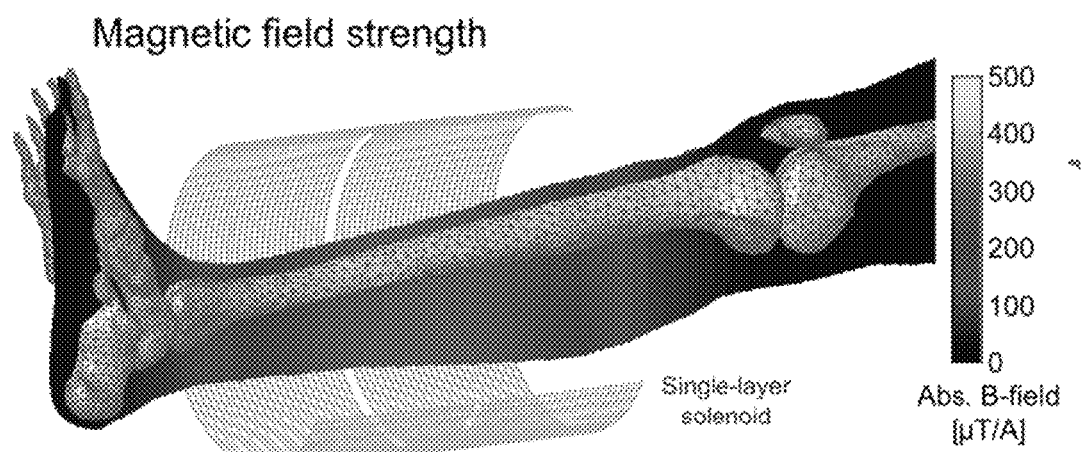
FIG. 13A shows magnetic field strength in a leg stimulation coil in accordance with an aspect of the present disclosure.
Figure 13B:
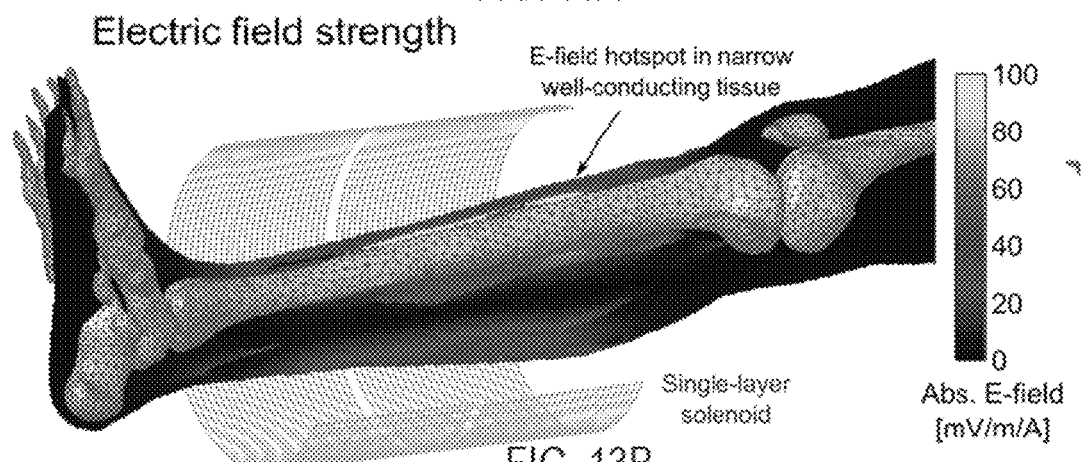
FIG. 13B shows electric field strength in a leg stimulation coil in accordance with an aspect of the present disclosure.
Figure 13C:
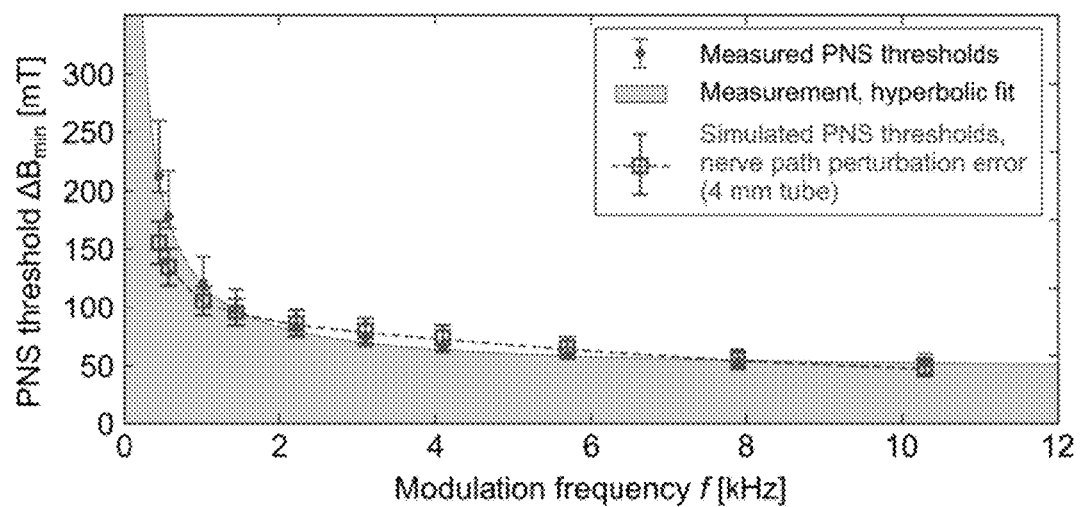
FIG. 13C shows measured and simulated PNS in the leg stimulation coil.

FIG. 13A shows magnetic field strength in a leg stimulation coil in accordance with an aspect of the present disclosure. FIG. 13B shows electric field strength in a leg stimulation coil in accordance with an aspect of the present disclosure. FIG. 13C shows measured and simulated PNS in the leg stimulation coil.

Figure 14A:
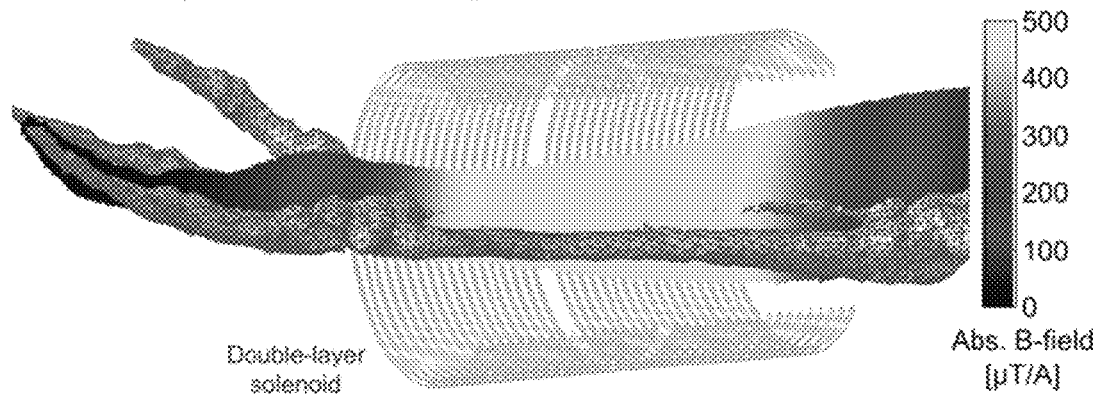
FIG. 14A shows magnetic field strength in an arm stimulation coil in accordance with an aspect of the present disclosure.
Figure 14B:
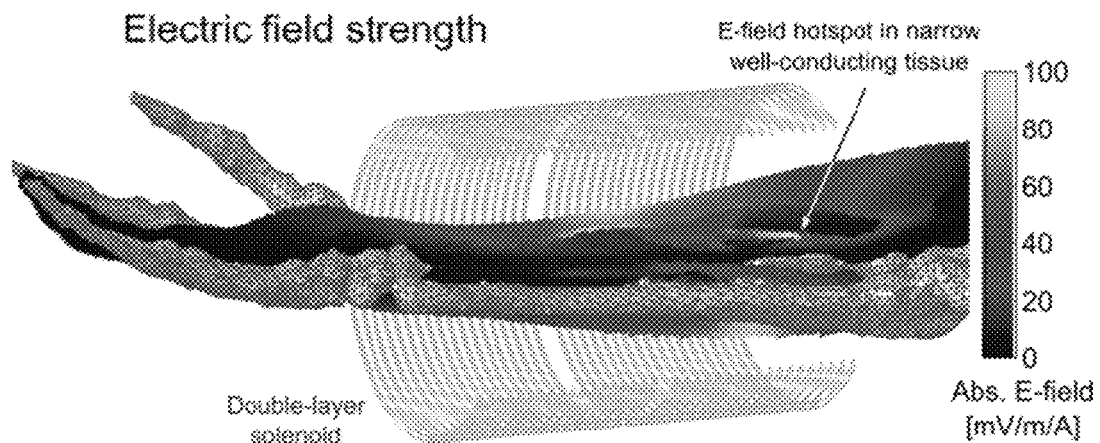
FIG. 14B shows electric field strength in an arm stimulation coil in accordance with an aspect of the present disclosure.
Figure 14C:
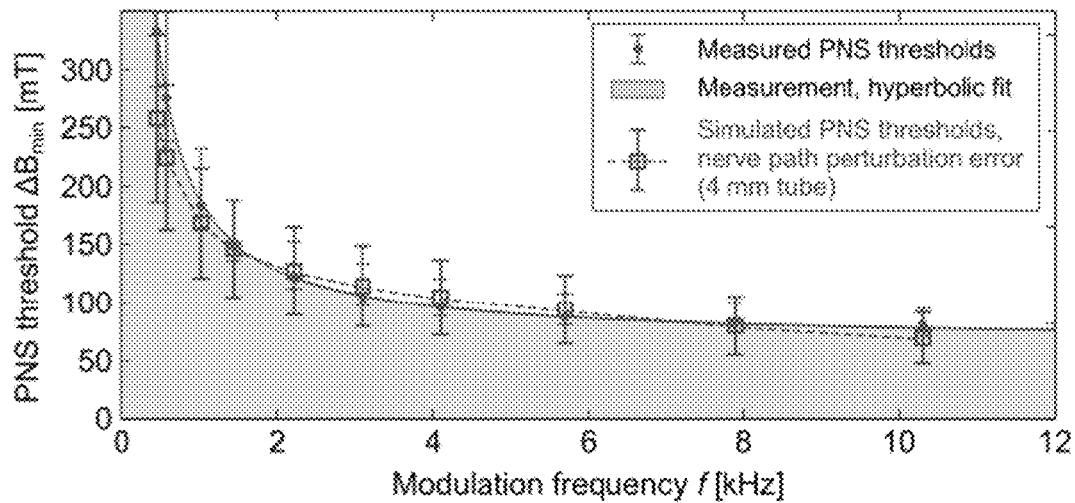
FIG. 14C shows measured and simulated PNS in the arm stimulation coil.

FIG. 14A shows magnetic field strength in an arm stimulation coil in accordance with an aspect of the present disclosure. FIG. 14B shows electric field strength in an arm stimulation coil in accordance with an aspect of the present disclosure. FIG. 14C shows measured and simulated PNS in the arm stimulation coil.

As shown in FIGS. 13A-C and 14A-C, the electric field magnitude is shown overlaid on the anatomical model. The measured values represent the median over 26 subjects (error bars indicate 25th and 75th percentile). The B-field generated by the modeled coil agrees well (within 1%) with the experimental value (measured values: 214 µT/A for the leg coil, 410 µT/A for the arm coil, simulated values: 211.86 µT/A for the leg coil, 407.1 µT/A for the arm coil). The electric field maps show that the electric field patterns are significantly modulated by the anatomical details of the model. Electric field hotspots occurred in tissues with low conductance, such as layers of fatty tissues separating different muscle fiber bundles and in regions where the conductivity is significant but the geometry narrows (e.g., the tibialis anterior muscle whose width becomes very small close to the shin bone region, arrow in FIG. 13B). Although the average measured PNS thresholds (gray region) from the 26 subjects and the simulated PNS thresholds (red curve) are in good overall agreement, there is some deviation in the low-frequency region of the PNS curves for both the leg and arm stimulations. However, the experimental values also exhibit increased variance in this frequency range. The imaging system repeated the PNS simulations using a range of spatial deformations applied to the most sensitive nerves, allowing the nerve segments to vary freely within a tube surrounding the unaltered nerve segment. For a tube radius of 2 mm (4 mm) the PNS thresholds computed for 20 deformed nerve segments in the arm showed a standard deviation of 15% (30%). The leg example showed an uncertainty of 6% and 14% for the 2 mm and 4 mm tube, respectively.

Figure 15A:
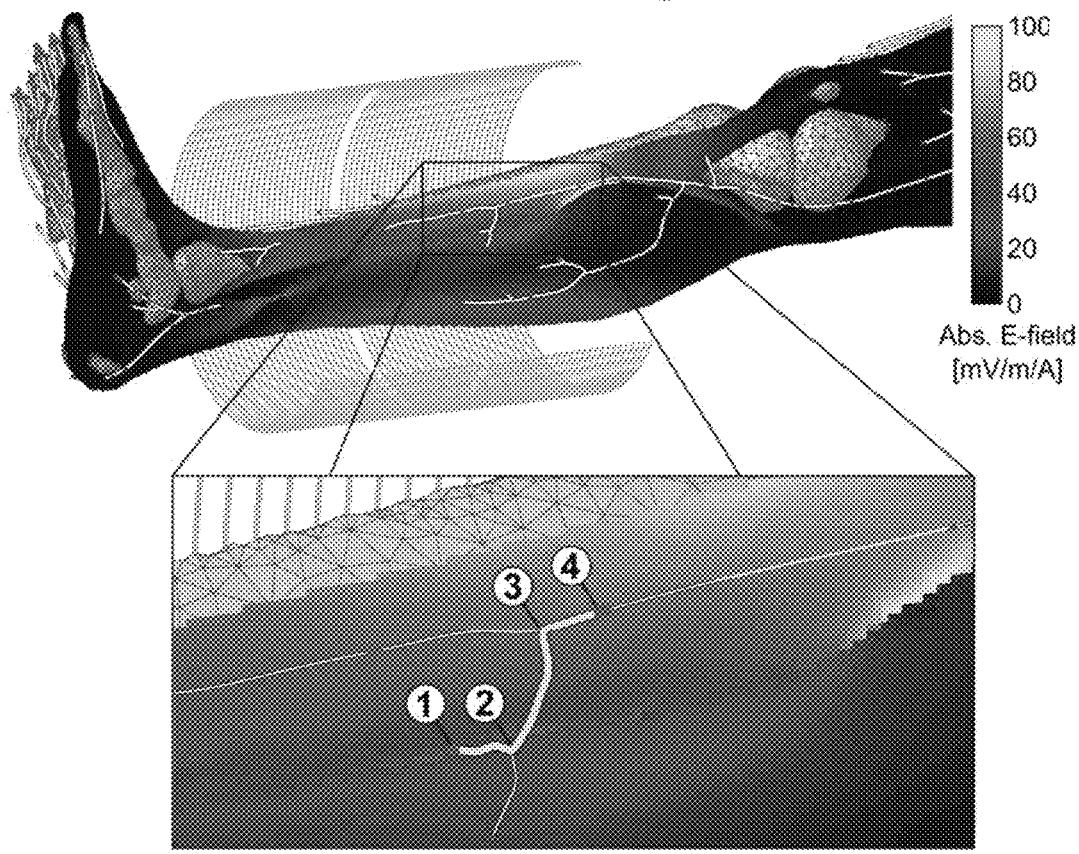
FIG. 15A shows electric field and nerve segments in a leg stimulation coil in accordance with an aspect of the present disclosure.
Figure 15B:
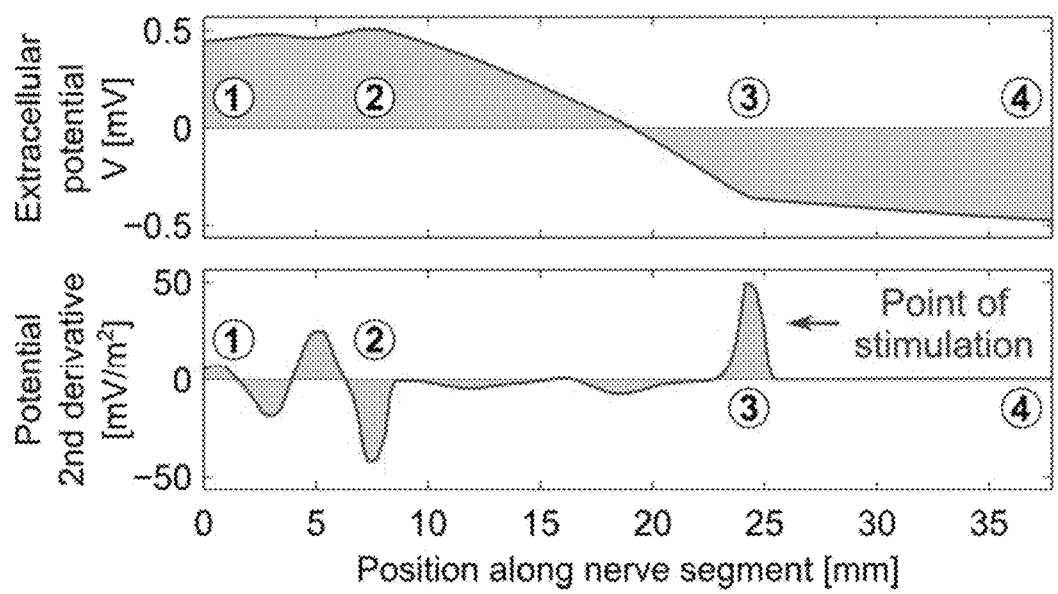
FIG. 15B shows nerve segments with smallest PNS threshold in a leg stimulation coil in accordance with an aspect of the present disclosure.

FIG. 15A shows electric field and nerve segments in a leg stimulation coil in accordance with an aspect of the present disclosure. FIG. 15B shows nerve segments with smallest PNS threshold in a leg stimulation coil in accordance with an aspect of the present disclosure.

Figure 16A:
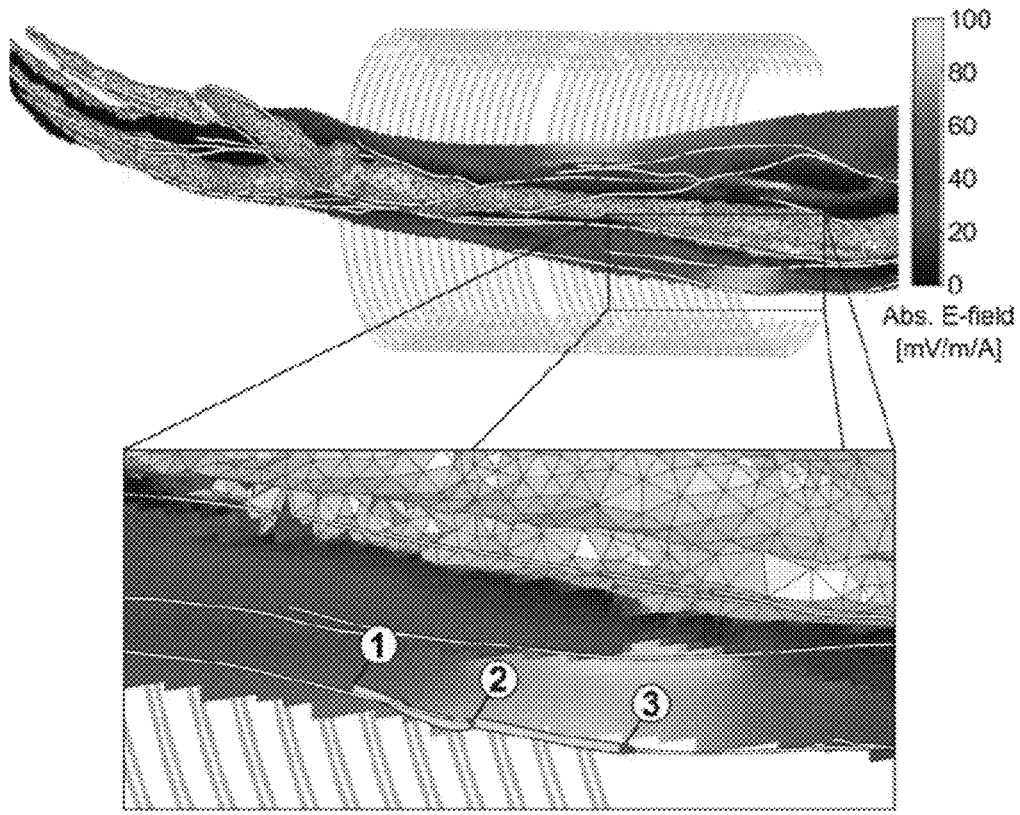
FIG. 16A shows electric field and nerve segments in an arm stimulation coil in accordance with an aspect of the present disclosure.
Figure 16B:
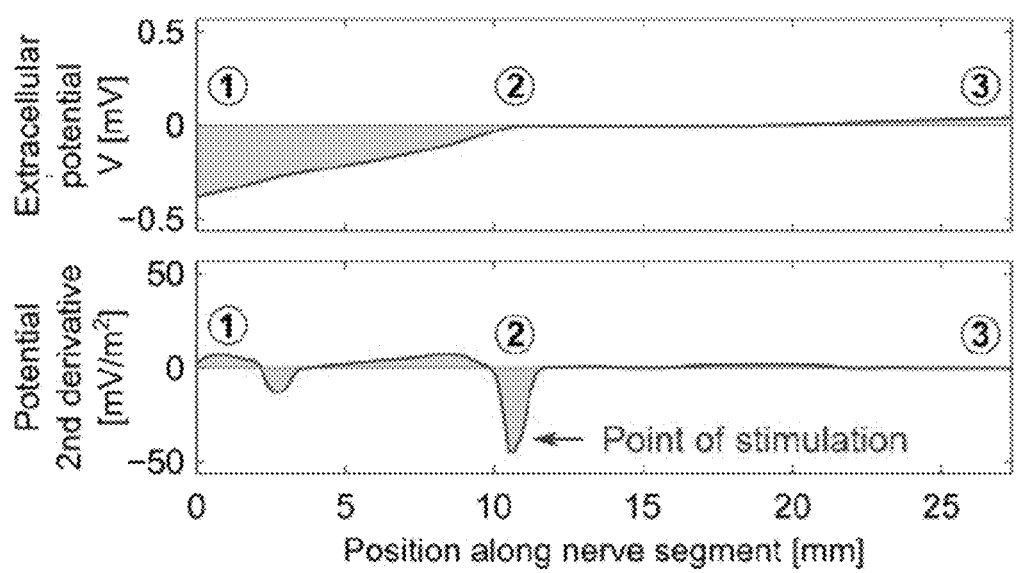
FIG. 16B shows nerve segments with smallest PNS threshold in an arm stimulation coil in accordance with an aspect of the present disclosure.

FIG. 16A shows electric field and nerve segments in an arm stimulation coil in accordance with an aspect of the present disclosure. FIG. 16B shows nerve segments with smallest PNS threshold in an arm stimulation coil in accordance with an aspect of the present disclosure.

FIGS. 15A-B and 16A-B illustrate the coil configurations and E-field maps, overlaid by the simulated nerve segments (red dots indicate boundaries of the individual nerve segments). In the zoomed images, the nerve segments with lowest stimulation thresholds are shown, which determine the PNS threshold curves. The bottom row of FIGS. 15B and 16B shows the electric potential and its second derivative of these two nerve segments (this is proportional to the amount of current entering of leaving the membrane). The kinks of these nerve segments in high E-field regions (positions 2 and 3 at the left, position 2 at the right) cause a sudden change in slope of the electric potential along the nerve segment, leading to a large inflow or outflow of current (peaks in the second derivative of the electrical potential).

In both the leg and arm situation, the stimulated nerve segments pass through a rather high E-field region (maximum E-field strengths along the excited segments were 66.6 mV/m/A in the leg and 47.7 mV/m/A in the arm). However, it is the high curvature of these nerve segments that plays a major factor in making these segments particularly sensitive to the applied E-field.

Figure 17:
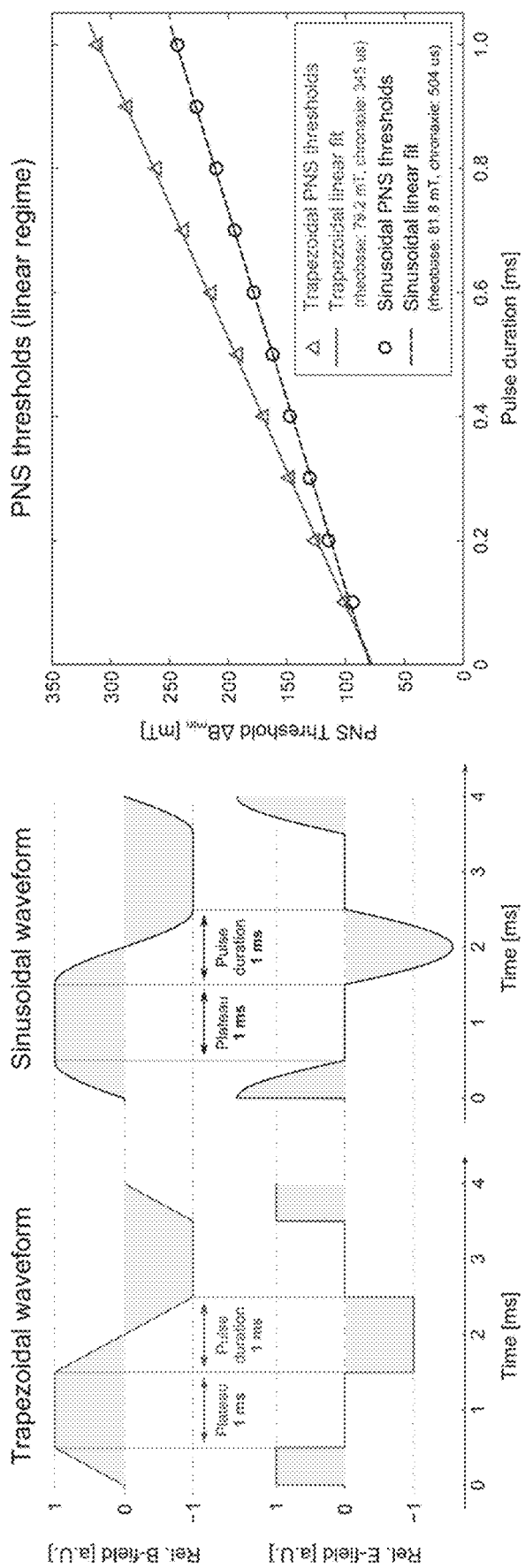
FIG. 17 shows the trapezoidal and sinusoidal waveforms B-field waveforms and the resulting E-field pulses and the resulting PNS thresholds as a function of pulse duration.

FIG. 17 shows the trapezoidal and sinusoidal waveforms studied and the pulse durations during which dB/dt (and thus an electric field) is present. FIG. 17 also shows the PNS thresholds for the arm coil as a function of pulse duration as well as the linear fit. The MRG neurodynamic model used in this work reproduces the increase of the PNS thresholds for trapezoidal pulses. The linear fit of the sinusoidal ($R^2$=0.9913) and trapezoidal thresholds ($R^2$=0.9947) reveals chronaxie times of 504 μs and 345 μs, respectively, which is in very good agreement with experimental data.

The disclosure provides a simulation framework for estimating the PNS thresholds for electromagnetic coils such as an MRI gradient coil or MPI drive coil operating in the kHz-range. In the first step, the imaging system calculates the electromagnetic fields created by the coil in a realistic body model, as has been reported in numerous previous studies. The imaging system then models the effect of these fields on realistic nerve models, including the relative geometry between field and nerve. The full body peripheral nerve model incorporates the properties of the myelinated fibers allowing the non-linear effect of the fields on membrane potentials to be calculated. The modeled time-dependent waveform is increased in steps to identify the lowest applied field (and thus current amplitude) which initiates an action potential. The location of the stimulation can also be recorded. The method has been validated by comparing to the published experimental PNS threshold curves for two solenoid coil geometries.

The results of the sensitivity analysis to deformations of the nerves relative to other tissues in the model indicate that the model is sensitive to the nerve shape and location relative to other tissues to a level similar to the variability of the experimental data. Note that there are other sources of variability expected for the estimation of PNS thresholds such as variations in the placement of patients in the coil (non-biological), as well as electromagnetic tissue properties in vivo (biological). Another deviation between the simulated and experimental PNS threshold curves are their slightly different shapes (when plotted as a function of frequency). This is likely due to the fact that there are aspects of action potential initiation and propagation that are not yet fully captured by the MRG membrane model. The MRG model is, however, currently one of the most sophisticated nerve models available. The procedure can be updated when more detailed membrane models become available, and might also prove a useful tool for refining these models.

Other embodiments of the present disclosure may be possible to those skilled in the art, upon taking into consideration of the specification and practice of the invention disclosed herein. The present application is intended to cover any variations, uses, or adaptations of the present disclosure, which follow the general principles of the present disclosure and include the common general knowledge or conventional technical solution in the art without departing from the present disclosure. The specification and embodiments are exemplified, and the true scope and spirit of the present disclosure can be indicated by the following claims.

Understandably, the present disclosure is not limited to the precise examples or embodiments described above and shown in the enclosed drawings, and various modifications and changes may be made without departing from the scope thereof. The scope of the present disclosure is limited only by the appended claims.

What is claimed is:

1. An imaging system comprising: a magnet system configured to generate a static magnetic field about at least a region of interest (ROI) of a subject arranged in the imaging system; at least one gradient coil configured to establish at least one magnetic gradient field with respect to the static magnetic field; a radio frequency (RF) system configured to deliver excitation pulses to the subject; a computer system programmed to: receive coil parameters that include current related to at least one radio frequency (RF) coil identified in an imaging pulse sequence to be performed in the imaging system; obtain a first model including a plurality of tissue types and corresponding electromagnetic properties in the ROI; obtain a second model indicating at least one of location, orientation, and physiological properties of one or more nerve tracks in the ROI, estimate a plurality of Peripheral Nerve Stimulation (PNS) thresholds in the ROI caused by the imaging pulse sequence applied in the imaging system using the first model, the second model, a nerve membrane model, and the coil parameters; estimate an extra concomitant field that reduces electric fields induced in the ROI by performing the pulse sequence using the coil parameters to be below at least a selected one of the PNS threshold during the imaging pulse sequence; and performing the imaging pulse sequence while generating the extra concomitant field that reduces electric fields induced in the ROI to maintain the electric fields produced in the ROI below at least a selected one of the PNS threshold.

2. The system of claim 1 wherein the first model comprises an anatomical tetrahedral mesh that models a plurality of tissue types and corresponding electromagnetic properties.

3. The system of claim 1 wherein the second model comprises a nerve fiber atlas that encodes location, orientation, and physiological properties of nerve tracks in a human body.

4. The system of claim 1 wherein the computer system is further programmed to compute electromagnetic fields in the ROI produced by the at least one gradient coil.

5. The system of claim 1 wherein the at least one gradient coil is a magnetic particle imaging (MPI) gradient coil, and the computer system is further programmed to compute electromagnetic fields in the ROI produced by the MPI gradient coil.

6. The system of claim 1 wherein the computer system is further programmed to estimate the plurality of the PNS thresholds by modulating electromagnetic fields, using the at least one RF coil, in amplitude in a first range and frequency in a second range until an action potential is detected by a membrane depolarization in the nerve membrane model.

7. The system of claim 6 wherein the first range is OmT to 100mT and the second range is 10 kHz to 200 kHz for the at least one gradient coil, wherein the at least one gradient coil is a magnetic particle imaging (MPI) gradient coil; and
wherein the first range is determined by a threshold of a magnetic resonance imaging (MRI) scanner and the second range is 0.1 kHz to 5 kHz for the at least one gradient coil.

8. The system of claim 1 wherein the computer system is programmed to generate magnetic and electric fields in the first model from a time-varying current applied to the at least one RF coil using an electromagnetic field simulation.

9. The system of claim 8 wherein the computer system is programmed to obtain an effective electric potential along a nerve fiber present in the one or more nerve tracks by projecting the electric fields onto the nerve fiber.

10. The system of claim 9 wherein the computer system is programmed to evaluate the nerve membrane model by providing the effective electric potential to the nerve membrane model; and
wherein the computer system is programmed to determine whether an action potential is initiated by analyzing an output of the nerve membrane model.

11. A method for assessing Peripheral Nerve Stimulation (PNS) in an imaging system, comprising:
receiving an imaging pulse sequence to be applied to at least a region of interest (ROI) of a subject arranged in the imaging system, the imaging pulse sequence identifying coil parameters that include current related to at least one coil;
obtaining a first model including a plurality of tissue types and corresponding electromagnetic properties in the ROI;
obtaining a second model indicating at least one of location, orientation, and physiological properties of one or more nerve tracks in the ROI;
estimating a plurality of PNS thresholds in the ROI caused by the imaging pulse sequence applied in the imaging system using the first model, the second model, a nerve membrane model, and the coil parameters;
estimating an extra concomitant field that reduces electric fields induced by performing the pulse sequence using the coil parameters to be below at least a selected one of the PNS threshold when performing the imaging pulse sequence using the coil parameters; and
reporting the extra concomitant field that reduces electric fields induced using the coil parameters below at least the selected one of the PNS threshold when performing the imaging pulse sequence using the coil parameters.

12. The method as recited in claim 11, wherein the first model comprises an anatomical tetrahedral mesh that models a plurality of tissue types and corresponding electromagnetic properties.

13. The method as recited in claim 11, wherein the second model comprises a nerve fiber atlas that encodes location, orientation, and physiological properties of nerve tracks in a human body.

14. The method of claim 11, wherein the at least one coil includes a magnetic resonance imaging (MM) gradient coil, and further comprising computing electromagnetic fields in the ROI produced by the magnetic resonance imaging (Mill) gradient coil.

15. The method of claim 11, wherein the at least one coil includes a magnetic resonance imaging (MM) gradient coil, and further comprising computing electromagnetic fields in the ROI produced by the magnetic particle imaging (MPI) gradient coil.

16. The method of claim 11, further comprising:
estimating the plurality of the PNS thresholds by modulating electromagnetic fields in amplitude in a first range and frequency in a second range using the at least one coil until an action potential is detected in the nerve membrane model.

17. The method of claim 16, wherein the first range is OmT to 100mT and the second range is 10 kHz to 200 kHz for the at least one coil, wherein the at least one coil is a magnetic particle imaging (MPI) gradient coil; and
wherein the first range is determined by a threshold of a magnetic resonance imaging (Mill) scanner and the second range is 0.1 kHz to 5 kHz for the at least one coil.

18. The method of claim 11, further comprising:
generating magnetic and electric fields in the first model from a time-varying current applied to the at least one coil using an electromagnetic field simulation.

19. The method of claim 18, further comprising:
obtaining an effective electric potential along a nerve fiber present in the one or more nerve tracks by projecting the electric fields onto the nerve fiber.

20. The method of claim 19, further comprising:
evaluating the nerve membrane model by providing the effective electric potential to the nerve membrane model; and
determining whether an action potential is initiated by analyzing an output of the nerve membrane model.

* * * * *

UNITED STATES PATENT AND TRADEMARK OFFICE
CERTIFICATE OF CORRECTION

PATENT NO. : 11,679,254 B2
APPLICATION NO. : 15/811588
DATED : June 20, 2023
INVENTOR(S) : Lawrence Wald et al.

It is certified that error appears in the above-identified patent and that said Letters Patent is hereby corrected as shown below:

In the Specification

Column 2, Line 30, "Vext" should be --$V_{ext}$--.

Column 9, Line 40, "Vext" should be --$V_{ext}$--.

Column 9, Line 41, "Vext" should be --$V_{ext}$--.

Column 9, Line 52, "Vext" should be --$V_{ext}$--.

Column 10, Line 28, "Vext" should be --$V_{ext}$--.

In the Claims

Claim 14, Column 18, Line 16, "(MM)" should be --(MRI)--.

Claim 14, Column 18, Line 18, "(Mill)" should be --(MRI)--.

Claim 15, Column 18, Line 21, "(MM)" should be --(MRI)--.

Claim 17, Column 18, Line 36, "(Mill)" should be --(MRI)--.

Signed and Sealed this
Twenty-ninth Day of August, 2023

Katherine Kelly Vidal
*Director of the United States Patent and Trademark Office*